US011717235B2

United States Patent
Shay et al.

(10) Patent No.: US 11,717,235 B2
(45) Date of Patent: Aug. 8, 2023

(54) SYSTEM AND METHOD FOR BIOMETRIC MEASUREMENTS

(71) Applicant: Blumio, Inc., San Francisco, CA (US)

(72) Inventors: Oliver Hao-Yuan Shay, San Francisco, CA (US); Lillian Lei Dai, San Francisco, CA (US)

(73) Assignee: ATCOR MEDICAL PTY. LTD., West Ryde (AU)

( * ) Notice: Subject to any disclaimer, the term of this patent is extended or adjusted under 35 U.S.C. 154(b) by 182 days.

(21) Appl. No.: 16/833,421

(22) Filed: Mar. 27, 2020

(65) Prior Publication Data

US 2020/0222011 A1 Jul. 16, 2020

Related U.S. Application Data

(62) Division of application No. 15/337,127, filed on Oct. 28, 2016, now abandoned.

(60) Provisional application No. 62/247,379, filed on Oct. 28, 2015.

(51) Int. Cl.
*A61B 5/00* (2006.01)
*A61B 5/021* (2006.01)
*A61B 5/05* (2021.01)
*G16H 40/67* (2018.01)

(52) U.S. Cl.
CPC ............ *A61B 5/7285* (2013.01); *A61B 5/021* (2013.01); *A61B 5/05* (2013.01); *A61B 5/721* (2013.01); *A61B 5/7225* (2013.01); *G16H 40/67* (2018.01)

(58) Field of Classification Search
CPC ....... A61B 5/7285; A61B 5/05; A61B 5/7225; A61B 5/721; A61B 5/021; G06F 19/3418
See application file for complete search history.

(56) References Cited

U.S. PATENT DOCUMENTS

| 4,958,638 A | 9/1990 | Sharpe et al. |
| 8,298,141 B2 | 10/2012 | Chen et al. |
| 9,134,404 B2 | 9/2015 | Lee et al. |
| 2006/0094937 A1* | 5/2006 | Immoreev .......... A61B 5/02438 600/301 |
| 2009/0209850 A1 | 8/2009 | Tao et al. |
| 2010/0179421 A1 | 7/2010 | Tupin |
| 2011/0089894 A1 | 4/2011 | Soar |
| 2012/0010609 A1 | 1/2012 | Deem et al. |

(Continued)

FOREIGN PATENT DOCUMENTS

CN 101371785 A 2/2009

OTHER PUBLICATIONS

International Search Report and Written Opinion for PCT Application No. PCT/US2019022531 dated Jul. 19, 2019.

*Primary Examiner* — Joel Lamprecht
(74) *Attorney, Agent, or Firm* — Andrus Intellectual Property Law, LLP

(57) ABSTRACT

A system and method for evaluating cardiovascular-related health of a user including an RF sensor device configured to transmit incident pulse signals towards the user, and to receive reflected pulse signals for generating a reflected pulse signal dataset, a pulse signal modification module configured to modify the reflected pulse signal dataset, and a processing system communicably coupled to the RF sensor device and the pulse signal modification module, the processing system configured to generate a cardiovascular parameter for the user based on the modified reflected pulse signal dataset.

6 Claims, 25 Drawing Sheets

(56) References Cited

U.S. PATENT DOCUMENTS

| | | |
|---|---|---|
| 2013/0030257 A1 | 1/2013 | Nakata et al. |
| 2013/0190599 A1 | 7/2013 | Wyeth et al. |
| 2014/0062822 A1 | 3/2014 | Tseng |
| 2014/0343393 A1 | 11/2014 | Lee et al. |
| 2015/0018676 A1 | 1/2015 | Barak |
| 2015/0031967 A1* | 1/2015 | LeBoeuf ............... A61B 5/681 600/300 |
| 2015/0073201 A1 | 3/2015 | Rogachefsky et al. |
| 2015/0254414 A1 | 9/2015 | Patel |
| 2015/0359436 A1 | 12/2015 | Shim et al. |
| 2017/0119318 A1 | 5/2017 | Shay et al. |

* cited by examiner

Inside View

SYSTEM AND METHOD FOR BIOMETRIC MEASUREMENTS

CROSS-REFERENCE TO RELATED APPLICATIONS

This application is a divisional of U.S. Non-Provisional patent application Ser. No. 15/337,127 filed 28 Oct. 2016, which claims the benefit of U.S. Provisional Application Ser. No. 62/247,379 filed 28 Oct. 2015, which is herein incorporated in its entirety by this reference.

TECHNICAL FIELD

The present invention relates to a system, apparatus and a method for biometric measurements of a subject, and more particularly to biometric measurements that utilize a sensor based on radio frequency (RF) detection and ranging technology.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview

Figure 1:
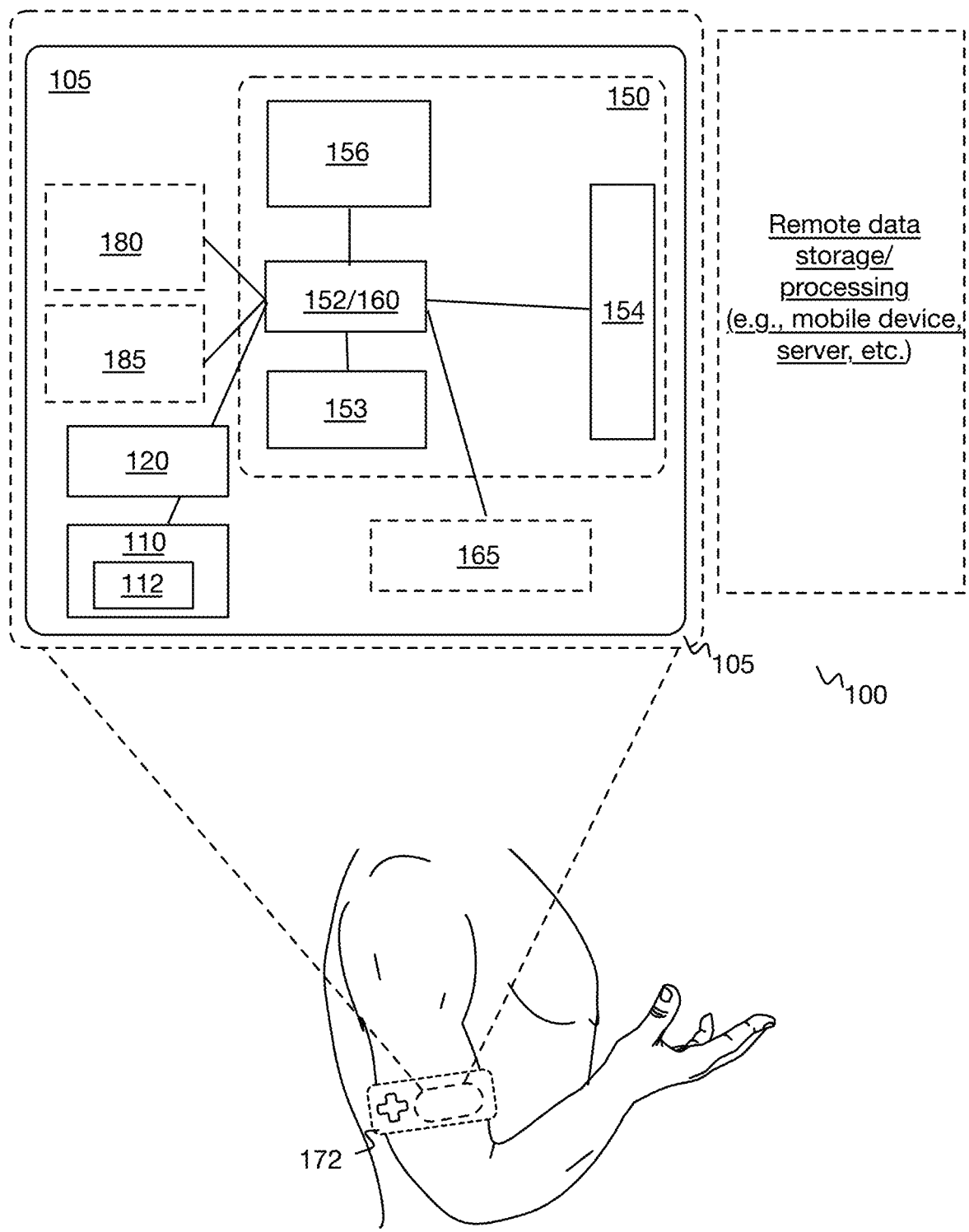
FIG. 1 is a schematic representation of a variation of an embodiment of a system.

As shown in FIG. 1, an embodiment of a system for evaluating cardiovascular-related health of a user can include a radio frequency (RF) sensor device operable to transmit incident signals (e.g., pulse signals) towards the user, and to receive reflected signals (e.g., pulse signals) for generating a reflected signal dataset; a signal modification module operable to modify the reflected signal dataset; and a processing and control system communicably coupled to the signal modification module, the processing and control system operable to generate a biometric measurement result for the user based on the modified reflected signal dataset.

In a variation, a system for evaluating cardiovascular-related health of a user includes a signal generator operable to generate a set of signals; a first and a second RF sensor device separated by a distance, each RF sensor device positioned proximal an interior face of a housing, and each RF sensor device operable between: a transmission mode where the RF sensor device transmits first incident signals derived from the set of signals towards a first artery of the user, and a receiving mode where the RF sensor device receives first reflected signals for generating a first reflected signal dataset; a delay module electrically coupled to the signal generator, and operable to generate a first delayed signal dataset derived from the set of signals with a first delay setting; a detector module (e.g., phase detector module) electrically coupled to the first and second RF sensor devices and the delay module, and operable to generate a first detected signal dataset (e.g., phase detected signal dataset) from mixing the first reflected pulse signal dataset with the first delayed pulse signal dataset; and a processing and control system communicably coupled to the pulse signal generator and the delay module, and operable between: a control mode where the processing and control system controls the signal generator and the delay module, a parameter determination mode where the processing and control system determines the first delay setting, and an output generation mode where the processing and control system generates a cardiovascular parameter for the user based on the first phase detected pulsed signal dataset and the distance between the first and second RF sensor devices.

The system functions to leverage an RF-based approach to non-invasively determining one or more biometric measurement results (e.g., cardiovascular parameters) describing the health of one or more users. The system can additionally or alternatively function to improve signal quality of signals collected by the RF system, such as through processing collected signals into a suitable form for generating accurate cardiovascular parameters based on the modified signals.

2. Benefits

In specific examples, the system and/or method can confer several benefits over conventional methodologies used for determining cardiovascular parameters such as blood pressure and heart rate. In specific examples, the system and/or method can perform one or more of the following:

First, the technology can dynamically improve the signal quality of signal datasets derived from the RF system and used in determining cardiovascular parameters. For example, the technology can continuously update parameters (e.g., delay values for delaying signals, delay line settings, weighting parameters, outlier filtering parameters, etc.) affecting signal quality before, during, and/or after sessions of RF sensor device activity (e.g., transmission of incident signals towards an artery of the user, receipt of reflected signals, etc.). As such, the technology can accommodate for variables affecting consistent signal quality, including user variations (e.g., different physiology, different motion, different ways of operating the RF system, etc.), RF system variations (e.g., different orientations of the RF sensor device, different arteries at which measurements are collected, etc.), and/or other variations.

Second, the technology can leverage an RF system including multiple RF sensor devices configured to transmit and receive signals at different locations of an artery, and/or at different arteries. For example, the RF system can include a first RF sensor device configured to collect reflected signals at a first location of a brachial artery, and a second RF sensor device configured to collect reflected signals at a second location of a brachial artery. Signal datasets collected at disparate locations can be used in evaluating body movement-related data (e.g., tissue movement-related data, respiration, heartbeat, arterial motion, stroke volume, pulse parameters such as pulse transit time and pulse wave velocity, etc.), from which cardiovascular parameters (e.g., heart beat metrics, blood pressure metrics, pulse rate metrics, physical activity metrics, metrics correlated with cardiovascular-related health, pulse oximetry metric, arterial metrics, respiration metrics, etc.) can be determined. The cardiovascular parameters can be used in a range of health and fitness applications, such as health monitoring, sports coaching, diagnosis and prediction of certain disease conditions such as cardiovascular related conditions (e.g. hypertension, atherosclerosis, arrhythmia, peripheral artery disease, aortic dissection, blood vessel insufficiency, pulmonary disease) and health-related emergency alerts. The RF system (e.g., based on RF detection and ranging) can be compact, non-invasive, and enable continuous monitoring of cardiovascular parameters, overcoming issues of inconvenience, discomfort, lack of adherence, and other issues associated with, for example, a blood pressure cuff. Further, the RF system can be resilient to variables (e.g., ambient light, presence of tattoos, perspiration at site of measurement, etc.) affecting signal quality for non-cuff based systems.

Third, the technology can continuously monitor cardiovascular parameters. For example, blood pressure data can be collected at a beat-to-beat granularity with greater than 10,000 samples collected per second. Cardiovascular parameter monitoring can additionally or alternatively be dynamically triggered (e.g., in response to detecting an inactive user state based on motion data collected at a motion sensor of the RF system).

The technology can, however, provide any other suitable benefit(s) in the context of using an RF system for detecting one or more cardiovascular parameters.

3. System

As shown in FIG. 1, the system 100 can include: an RF sensor device 110 configured to transmit incident signals (e.g., incident pulse signals) towards the user, and to receive reflected signals for generating a reflected signal dataset; a signal modification module 120 configured to modify the reflected signal dataset; a processing and control system 150 communicably coupled to the RF sensor device 110 and the signal modification module 120, the processing and control system 150 configured to generate a cardiovascular parameter for the user based on the modified reflected signal dataset; and a signal generator 160 configured to generate signals.

In some variations, the system 100 can additionally or alternatively include a conditioning module 140 configured to process signal datasets, a supplemental sensor module 165, a housing 170, and/or any other suitable component.

One or more RF sensor devices 105, signal modification modules 120, processing and control systems 150, signal generators 160, conditioning modules 140, and/or supplemental sensors 165 can be included in an RF system 105, which can additionally or alternatively include a housing 170 retaining the preceding components. However, in examples, the system 100 can include components outside of the RF system, such as a remote server and/or a user mobile phone 310 of the processing and control system 150 operable to generate a cardiovascular parameter from a signal dataset.

3.1 RF Sensor Device

As shown in FIG. 1, the system 100 can include an RF sensor device 110 operable to transmit incident signals towards the user, and to receive reflected signals for generating a reflected signal dataset. The RF sensor device 110 functions to transmit and/or receive signals for downstream processing in generating biometric measurement results (e.g., cardiovascular parameters) for a user. The RF sensor device 110 preferably includes one or more antennas 112 (e.g., transmit antenna 114, receive antenna 116, etc.), but can additionally or alternatively include one or more signal modification modules 120 and/or conditioning modules 140.

The RF sensor device 110 is preferably operable across (e.g., can operate in any of the modes in parallel, in serial, etc.), a transmission mode (e.g., half-duplex, full-duplex) where the RF sensor device 110 transmits incident signals (e.g., derived from a set of signals generated at a signal generator 160), and a receiving mode (e.g., half-duplex, full-duplex) where the RF sensor device 110 receives reflected signals (e.g., for generating a reflected signal dataset). The RF sensor device 110 is preferably configured to perform near-field (NF) sensing, but can additionally or alternatively perform mid-field and/or far-field sensing. Signals transmitted by the RF sensor device 110 are preferably RF signals, but can alternatively be other signal types possessing other suitable frequencies or signal characteristics. The transmitted signals are preferably generated by a signal generator (e.g., a pulse signal generator 160) of the RF system 105, but any suitable signals can be transmitted. Incident signals, reflected signals, and/or any suitable signal can be continuous wave, substantially continuous, discrete, pulse signals, other wave signals and/or any suitable signals. Approaches described in relation to pulse signals and/or pulse signal datasets can be analogously applied to any suitable signal type.

The RF sensor device 110 is preferably communicably coupled (e.g., electrically coupled, electrically connected, wirelessly coupled) to a processing and control system 150 configured to control the RF sensor device 110 (e.g., by communicating with the RF sensor device 110 to initiate signal acquisition, by independently controlling different RF sensor devices 110 and/or different antennas 112 of an RF sensor device 110, etc.), to receive pulse signal data (e.g., reflected pulse signal datasets, conditioned pulse signal datasets, etc.) collected by the RF sensor device 110 (e.g., at a receive antenna 116), and/or perform other suitable functions in relation to the RF sensor device 110. In an example, the RF sensor device 110 can include a wireless communications module 154 configured to communicate with a remote processing and control system 150 (e.g., a remote processing subsystem 152 within a housing 170 retaining the RF sensor device 110, a remote server distant from the RF system 105 and/or user, etc.). In a specific example, the RF sensor device 110 can transmit pulse signal data to a processing subsystem 152 housed within the RF system 105, and the processing subsystem 152 can generate cardiovascular parameters for presentation at the RF system 105 and/or a distinct user device (e.g., a user mobile phone 310, a band 172, etc.). In another specific example, pulse signal data sampled at the RF sensor device 110 can be transmitted to a processing subsystem 152 of a distinct user device (e.g., a user mobile phone 310, a band 172, etc.) and/or remote server, which can generate cardiovascular parameters for presentation at the RF system 105, and/or a distinct user device. In examples, signal processing can be fully or partially performed by other components, such as the processing and control system 150 (e.g., processing subsystems 152 of the RF system 105, processing subsystems 152 of a remote server, processing subsystems 152 of a distinct user device such as a user mobile phone 310, computer, medical device, exercise equipment, etc.).

The RF sensor device 110 is preferably positioned proximal an artery of the user in an alignment configuration during use (e.g., where the RF sensor device 110 is aligned with the target artery for transmitting pulse signals toward the target artery and receiving reflected signals). For example, in the alignment configuration, the RF system 105 is preferably worn by a user and/or positioned by a user at a location where the RF sensor device 110 is proximal the artery at which pulse signals are to be transmitted. In examples, the RF sensor device 110 is preferably positioned proximal an artery of the arm (e.g., a brachial artery, radial artery, ulnar artery, profunda brachii artery, anterior humeral circumflex artery, axillary artery, etc.) of the user, but can be positioned in relation to any suitable artery (e.g., carotid artery in the neck, etc.). Additionally or alternatively, the target for the transmitted signals can be a region of the chest, aorta, vein, and/or other physiological region exhibiting movement. However, the RF sensor device 110 can be positioned relative any physiological region in an alignment configuration and/or any suitable configuration.

Figure 4:
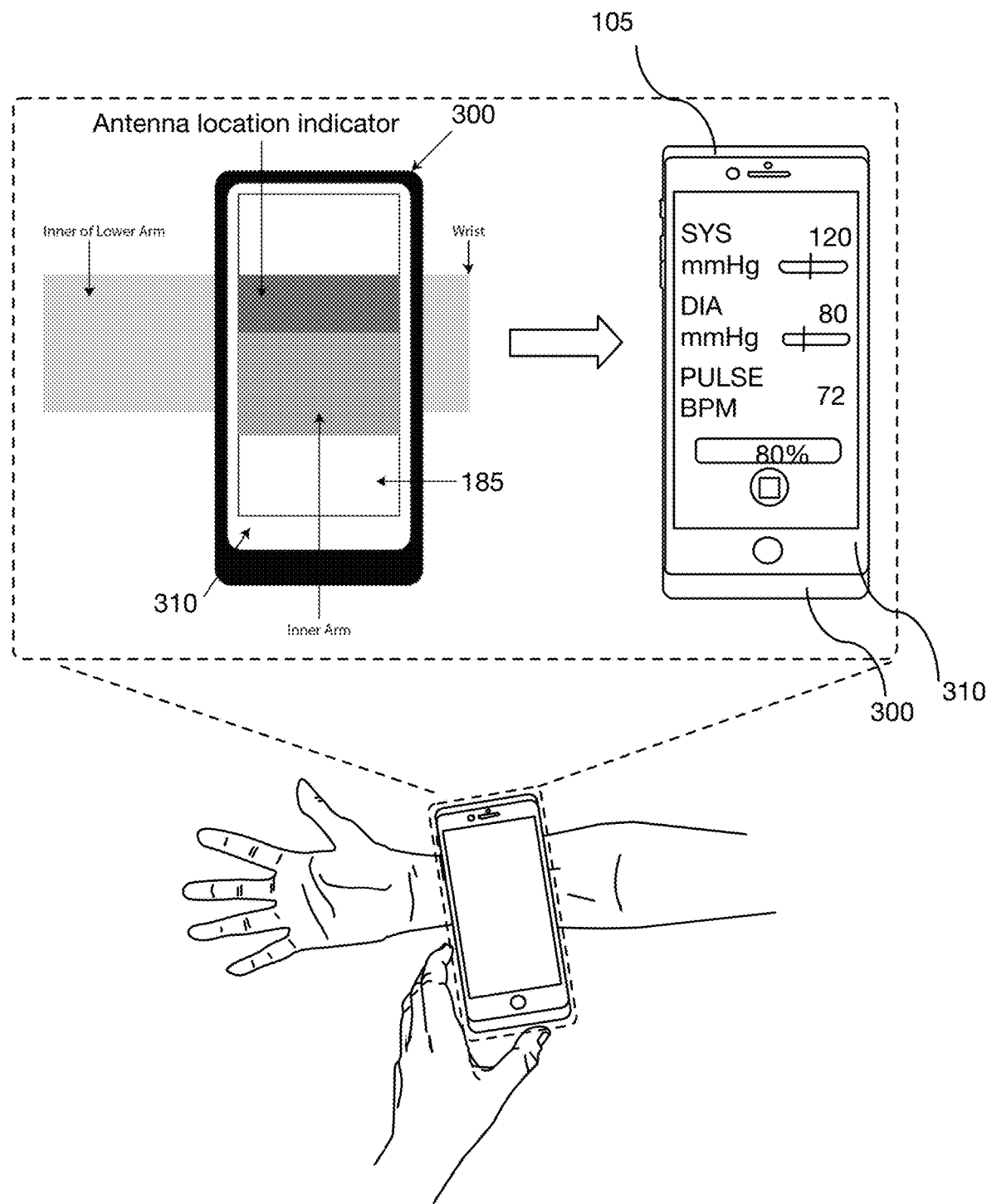
FIG. 4 is a schematic representation of a variation of an embodiment of a system.

In an example, the RF sensor device 110 can be positioned at or within an interior face (e.g., inside the RF system and facing housed components of the RF system) of the housing 170. As shown in FIG. 4, in this example, the interior face of the housing 170 can be proximal the target artery (e.g., the artery at which incident signals are transmitted) in an alignment configuration (e.g., where the RF sensor device 110 is aligned with the target artery for transmitting pulse signals toward the target artery and receiving reflected signals). However, the RF sensor device 110 can be positioned relative the housing 170 in any suitable manner.

Figure 2:
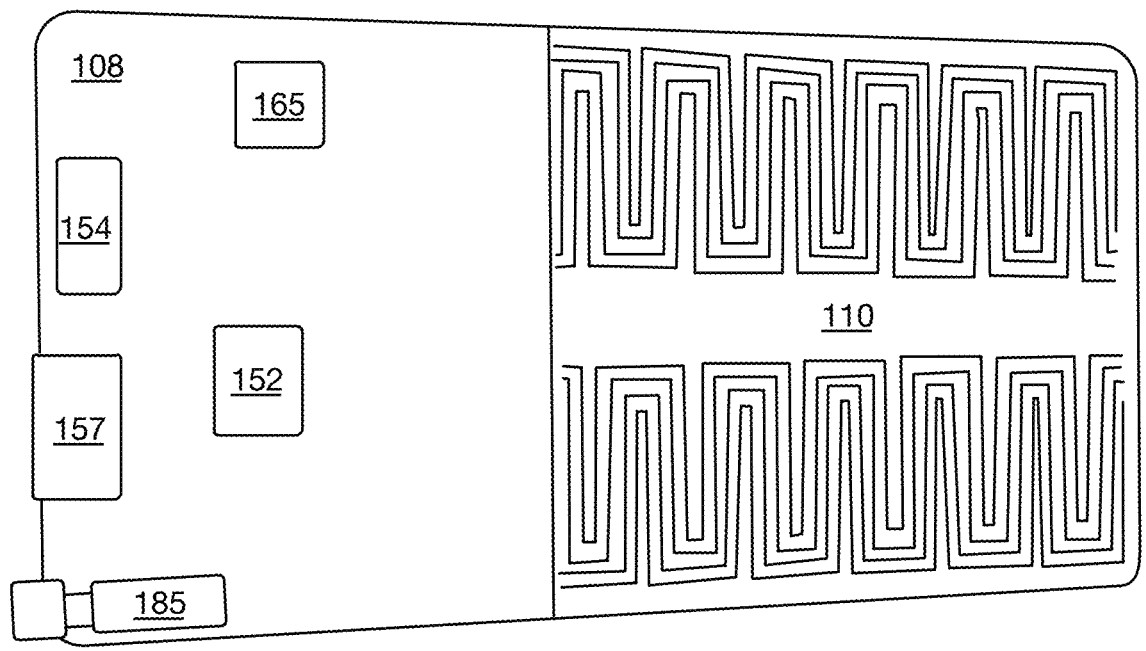
FIG. 2 is a schematic representation of a radio frequency system components implemented with a substrate in a variation of an embodiment of a system.

As shown in FIG. 2, circuitry components of the RF sensor device 110 can be integrated with a substrate 108 (e.g., a printed circuit board). In relation to the substrate, in an example, the RF sensor device 110 can be positioned proximal a first edge of the substrate 108, and distant an opposing second edge of the substrate 108 (e.g., where the processing and control system 150 is positioned). In this example, the RF sensor device 110 can be characterized by a rectangular form factor, but can embody any suitable shape. Additionally or alternatively, the RF sensor device 110 can be positioned at any suitable location relative a substrate 108, and/or be positioned substantially distant from a substrate 108.

The RF sensor device 110 is preferably constructed with flexible materials (e.g., configured to conform to the contour of a user's physiological region in examples where the RF system 105 is configured to be worn as a wearable biometric measurement device by the user). In a specific example, the RF sensor device 110 can be constructed with a flexible substrate 108, antenna 112, and housing 170. Additionally or alternatively, the RF sensor device 110 can be constructed with rigid materials and/or any suitable materials.

Figure 5:
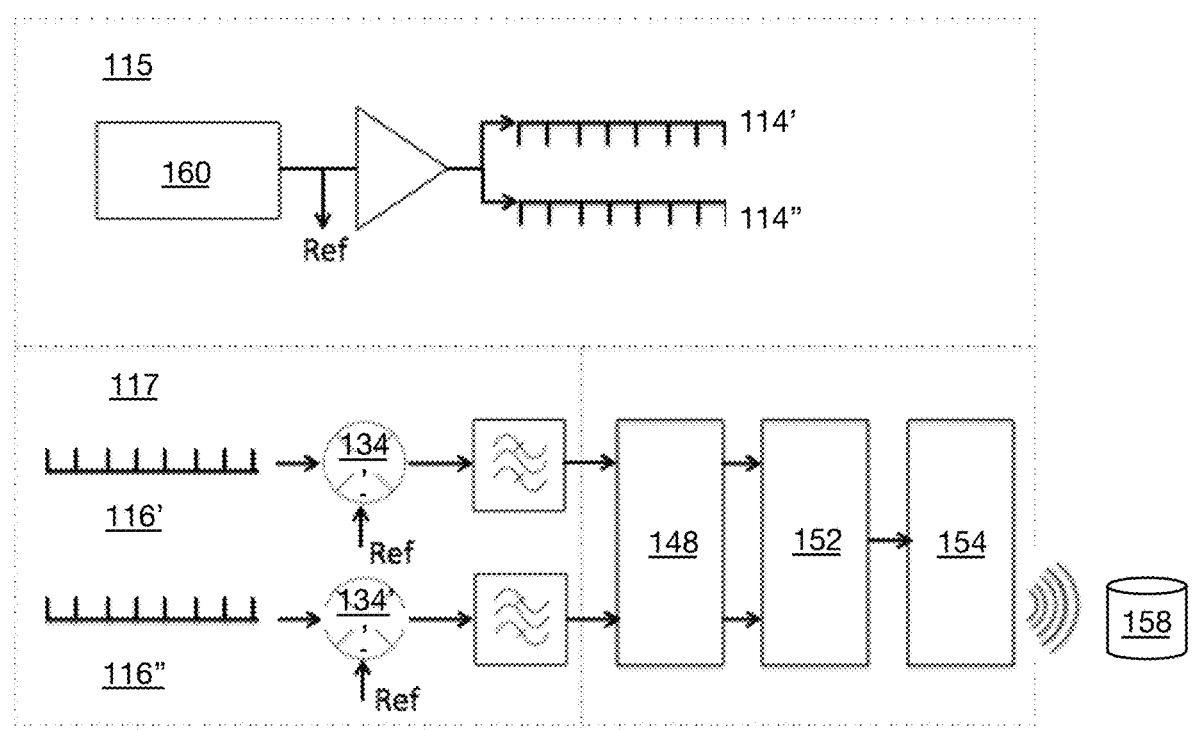
FIG. 5 is a schematic representation of processing flow in a variation of an embodiment of a system.

The RF system 105 can include any number of an RF sensor devices 110 (e.g., which can function to provide hardware redundancy, to collect different sets of pulse signal data, etc.). For example, in response to failure and/or malfunctioning of an RF sensor device 110, another RF sensor device 110 can be activated automatically or manually to ensure uninterrupted service or reduce system outage time (e.g., where an alert can be generated to notify appropriate personnel regarding the failure, or malfunction). Each RF sensor device 110 preferably includes at least one antenna 112, but can be otherwise configured. In a variation, the RF system 105 can include a first and a second RF sensor device 110''. In this variation, the first and second RF sensor devices 110 are preferably positioned at a known distance from each other, where the known distance can be used downstream in calculating pulse parameters from collected pulse signal datasets. In a specific example, as shown in FIG. 5, the first RF sensor device 110' can have a first transmit antenna 114' and a first receive antenna 116' positioned at a first region (e.g., of a substrate 108 where the first RF sensor device 110' is integrated), and the second RF sensor device 110'' can have a second transmit antenna 114'' and a second receive antenna 116'' positioned at a second region (e.g., of the substrate 108), where the first and the second regions are separated by a known distance. In an example, the first and the second RF sensor devices 110 can be electrically coupled (e.g., to transmit and/or receive control instructions and/or data between the RF sensor devices 110). In this or another example, the first RF sensor device 110' and/or second RF sensor device 110'' can be communicatively coupled to the processing and control system 150 and operable to receive control instructions from the processing and control system 150, operate based on the control instructions, and to transmit the control instructions to the second RF sensor device 110''. In variations where the first and second RF sensor devices 110', 110'' are associated with separate substrates, the first and second RF sensor devices 110 can have substantially similar and/or distinct geometries (e.g., similar or different dimensions), orientations (e.g., a first RF sensor device 110' with a transmit antenna 114 oriented towards an interior face of the housing 170 at a first angle, and a second RF sensor device 110'' with a transmit antenna 114 oriented towards the interior face at a second angle distinct from the first angle) construction materials (e.g., a first RF sensor device 110' constructed with flexible materials, a second RF sensor device 110'' constructed with rigid materials), locations (e.g., a first RF system 105' positioned proximal a processing and control system 150' integrated with a first substrate 108', and the second RF system 105'' positioned proximal a processing and control system 150'' integrated with a second substrate 108", etc.), and/or other suitable characteristics. However, multi-RF sensor device 110 configurations can be otherwise defined.

Additionally or alternatively, an RF sensor device 110 or set of RF sensor devices 110 can be configured in any suitable manner.

Figure 7:
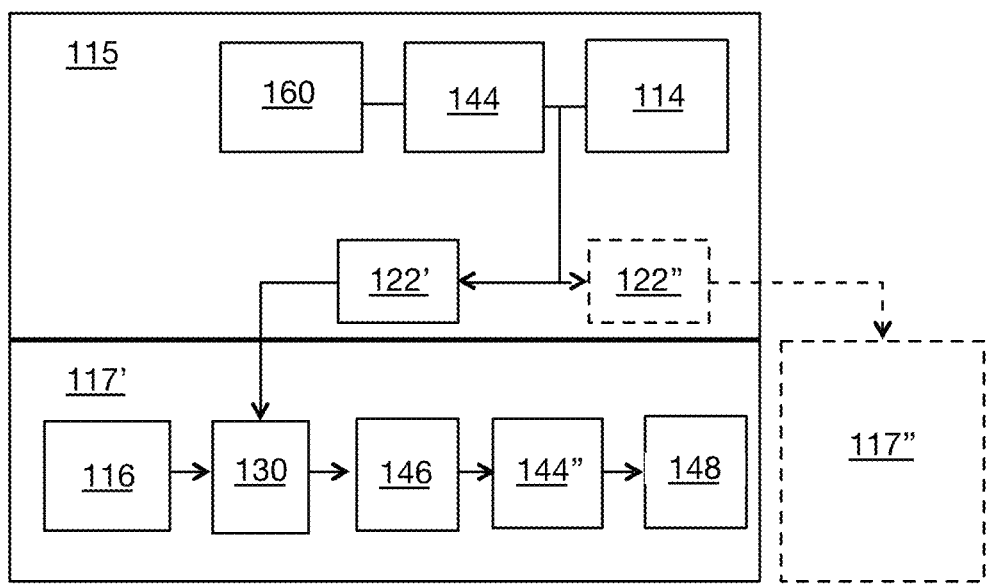
FIG. 7 is a schematic representation of processing flow in a variation of an embodiment of a system.

An RF sensor device 110 preferably includes one or more antennas 112. An antenna 112 can be configured to transmit signals (e.g., a transmit antenna 114) and/or receive signals (e.g., a receive antenna 116). In examples, the transmit and receive antennas 112 are distinct antenna 112 elements. Alternatively, an antenna 112 can be used for both transmit and receive activities through circuitry used for antenna 112 duplex operations. One or more antennas 112 can paired with and/or included in a transmitter block 115 and/or a receiver block 117, where one or more transmitter blocks 115 paired with one or more receiver blocks 117 can act as a transmit and receive chain. In an example, as shown in FIG. 7, the RF sensor device 110 can include a transmitter block 115 with a transmit antenna 114, and two receiver blocks 117', 117". In an example, the RF system 105 can include a plurality of transmit and receive chains. In specific examples, an RF sensor device 110 including a single transmit and receive chain can be configured to generate a heart rate parameter, and an RF sensor device 110 including two transmit and receive chains can be configured to generate a blood pressure parameter and/or heart rate parameter (e.g., where each transmit and receive chain can generate a heart rate parameter, and the heart rate parameters can be compared and rejected in response to differing more than a threshold amount).

The antennas 112 are preferably constructed with flexible materials, but can otherwise be semi-flexible, rigid, and/or constructed with other suitable materials. In relation to the housing 170, the antennas 112 are preferably positioned proximal an interior face of the housing 170, but can be otherwise positioned.

In variations, the RF sensor device 110 can include one or more orientation-adjustable antennas 112 controllable by the processing and control subsystem. In this variation, orientation-adjustable antennas 112 can be operable to adjust their corresponding signal transmission axis (e.g., by reorienting their position at the substrate 108, by an actuator of the RF system 105 actuating the orientation-adjustable antennas 112 into a different orientation, etc.). Additionally or alternatively, orientation-adjustable antennas can be included in an antenna array, where directionality of transmitted and received signals can be controlled by changing phase and/or phase amplitude of antenna elements of the antenna aray. However, orientation-adjustable antennas 112 can be otherwise configured. Additionally or alternatively, an antenna 112 or set of antennas 112 can be configured in any suitable manner.

Any number of RF sensor devices 110 can additionally or alternatively be included in the RF system 105.

3.2 Signal Modification Module

The system 100 can include a signal modification module 120 operable to modify the reflected signal dataset, which functions to modify signal data collected by the RF sensor device 110 in order to improve signal quality (e.g., with the delay module), and/or detect phase change between a reference signal and a reflected signal (e.g., with the mixer module). The signal modification module 120 additionally or alternatively specifically function to modify one or more amplitude parameters of signal data to improve signal quality. The signal modification module 120 can include one or more delay modules 121, detector modules 130, pulse shaper modules 142, dynamic amplification modules 144, and/or any other suitable components.

The signal modification module 120 is preferably operable to generate a modified signal dataset. The signal module is preferably coupled (e.g., electrically coupled, communicably coupled) to one or more RF sensor devices 110, but can alternatively be included in one or more RF sensor devices 110. In such examples, the signal module is preferably configured to receive one or more signal datasets (e.g., pulse signal datasets) collected at the RF sensor device 110, and to modify the signals in the one or more datasets. Additionally or alternatively, the signal module can be electrically coupled to a pulse signal generator 160 and configured to modify signals generated by the pulse signal generator 160.

Further, the signal modification module 120 is preferably electrically coupled to a processing and control system 150 configured to control the signal modification module 120. In examples, the processing and control system 150 can determine the parameters according to which the signal modification module 120 operates (e.g., determining delay values for the delay module 121), can activate and/or deactivate the signal modification module 120, can transmit and/or receive datasets from the signal modification module 120, and/or control the signal modification module 120 in any suitable manner. However, the signal modification module 120 can be electrically coupled and/or communicably coupled to any suitable component The signal modification module 120 is preferably implemented with hardware components, but can additionally or alternatively be implemented through software. The signal modification module 120 is preferably included in the RF system 105 (e.g., retained in the RF system 105 housing 170, sharing a baseboard integrating the RF sensor device 110 and/or processing and control system 150, etc.), but can additionally or alternatively include a remote server configured to modify signal data. The RF system 105 can include any number of signal modification modules 120.

Any number of signal modification modules 120 can additionally or alternatively be included in the RF system 105. However, a signal modification module 120 can be configured in any suitable manner.

3.2.A Delay Module

Figure 20:
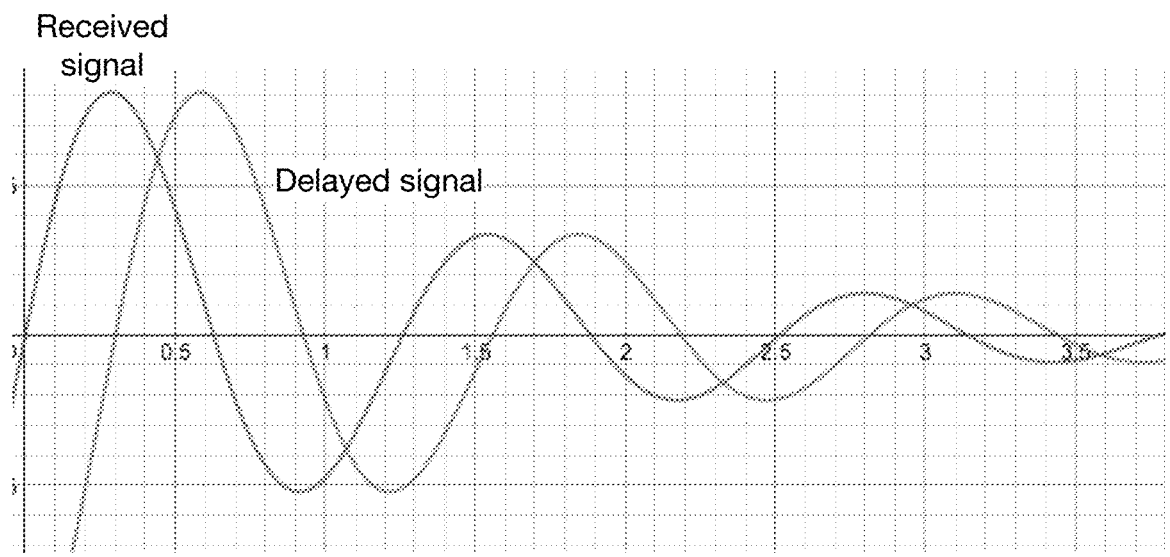
FIG. 20 is a schematic representation of a received signal and a delayed signal in a variation of an embodiment of a method.

The signal modification module 120 can include a delay module 121 functioning to delay one or more signals (e.g., as shown in FIG. 20).

The delay module 121 is preferably configured to generate one or more delayed pulse signal datasets by processing a pulse signal dataset according to a delay setting (e.g., delay value, delay line of a set of delay lines). The delay module 121 can include any one or more of: a potentiometer (e.g., digital potentiometer), a delay chip (e.g., a digital delay chip), a delay circuit (e.g., fixed delay lines with a switch 124, etc.), a phase shifter, software (e.g., executable by the processing and control system 150) and/or any suitable component configured to delay a pulse signal. The delay value can take any one or more forms including: a temporal indicator (e.g., microseconds, milliseconds, seconds, etc.), a pulse parameter modification (e.g., frequency unit, phase unit, etc.), and/or any suitable form describing a delay to apply to a pulse signal. Additionally or alternatively, the delay module can generate a delayed pulse signal dataset without a calculated delay value. For example, the delay module can include a delay circuit with a plurality of delay lines operable with one or more switches 124 by processing and control system 150, where the processing and control system 150 can iterate through operation of each delay line, evaluate signal quality, and select a delay line based on the signal quality. Pulse signal datasets that are delayed preferably include pulse signal data generated by a pulse signal generator 160 (e.g., after pulse width modulation), but can include any suitable pulse signal data.

The delay module 121 is preferably a dynamic delay module 121 configured to delay signal datasets based on dynamic delay values (e.g., dynamically determined by a processing and control system 150 controlling the delay module 121), but can additionally or alternatively include static delay properties (e.g., where a static delay value module 121 is configured to delay signal datasets based on a static delay value that is constant throughout the remainder of signal acquisition following determination of the static delay value such as through updating the delay value until a suitable signal amplitude is obtained, etc.).

Figure 6A:
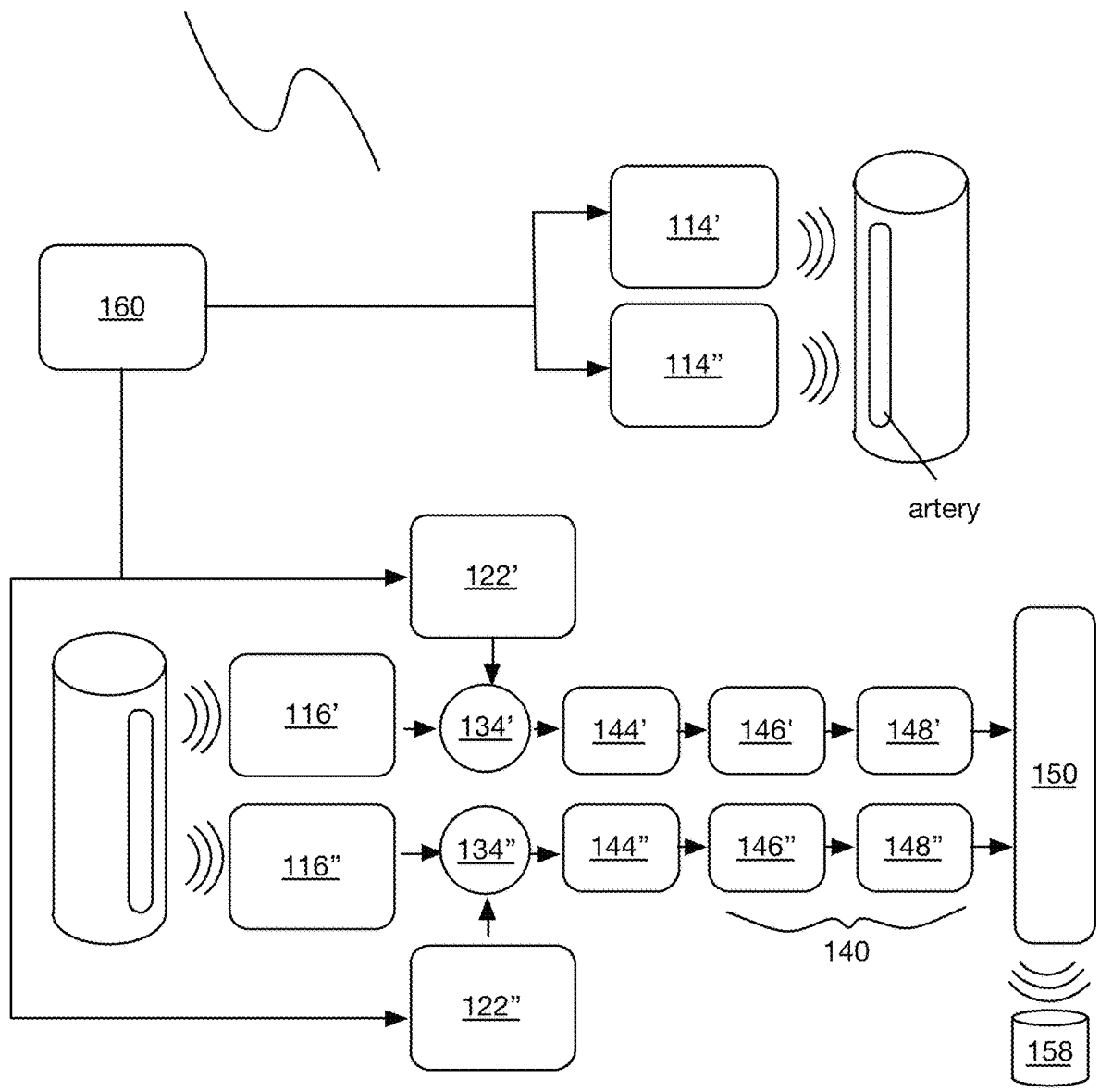
FIGS. 6A-6C are schematic representations of processing flows in variations of an embodiment of a system.

In a first variation, as shown in FIG. 6A, the delay module 121 can be an analog delay module 121 configured to perform analog delay on a signal dataset. In this variation, one or more pulse signals generated by a pulse signal generator 160 can be input (e.g., subsequent to conditioning by one or more conditioning modules 140) into one or more delay modules 121 (e.g., digital potentiometers) controlled by a processing and control system 150. In a specific example, a first and a second pulse signal dataset (e.g., generated by a pulse signal generator) can be respectively input into a first and a second transmit antenna 114', 114" for transmission as incident signals. The first and second pulse signal datasets can additionally or alternatively be input into a first and a second delay component 122', 122" of one or more delay modules 121 for generating a first and a second delayed signal dataset. Reflected signals reflected from the incident signals can be collected at a first and a second receive antenna, 116', 116" for generating a first and a second reflected signal dataset. The first delayed signal dataset and the first reflected signal dataset can be mixed at a first mixing component 134' to generate a first phase detected signal dataset, and the second delayed signal dataset and the second reflected signal dataset can be mixed at a second mixing component 134" to generate a second phase detected signal dataset. The phase detected signal dataset can be transmitted to one or more conditioning modules 140 (e.g., for subsequent transmission to a processing and control system 150), directly to a processing and control system 150 (e.g., for determining a biometric measurement result), and/or any suitable component. However analog delay modules 121 can be otherwise configured.

Figure 6B:
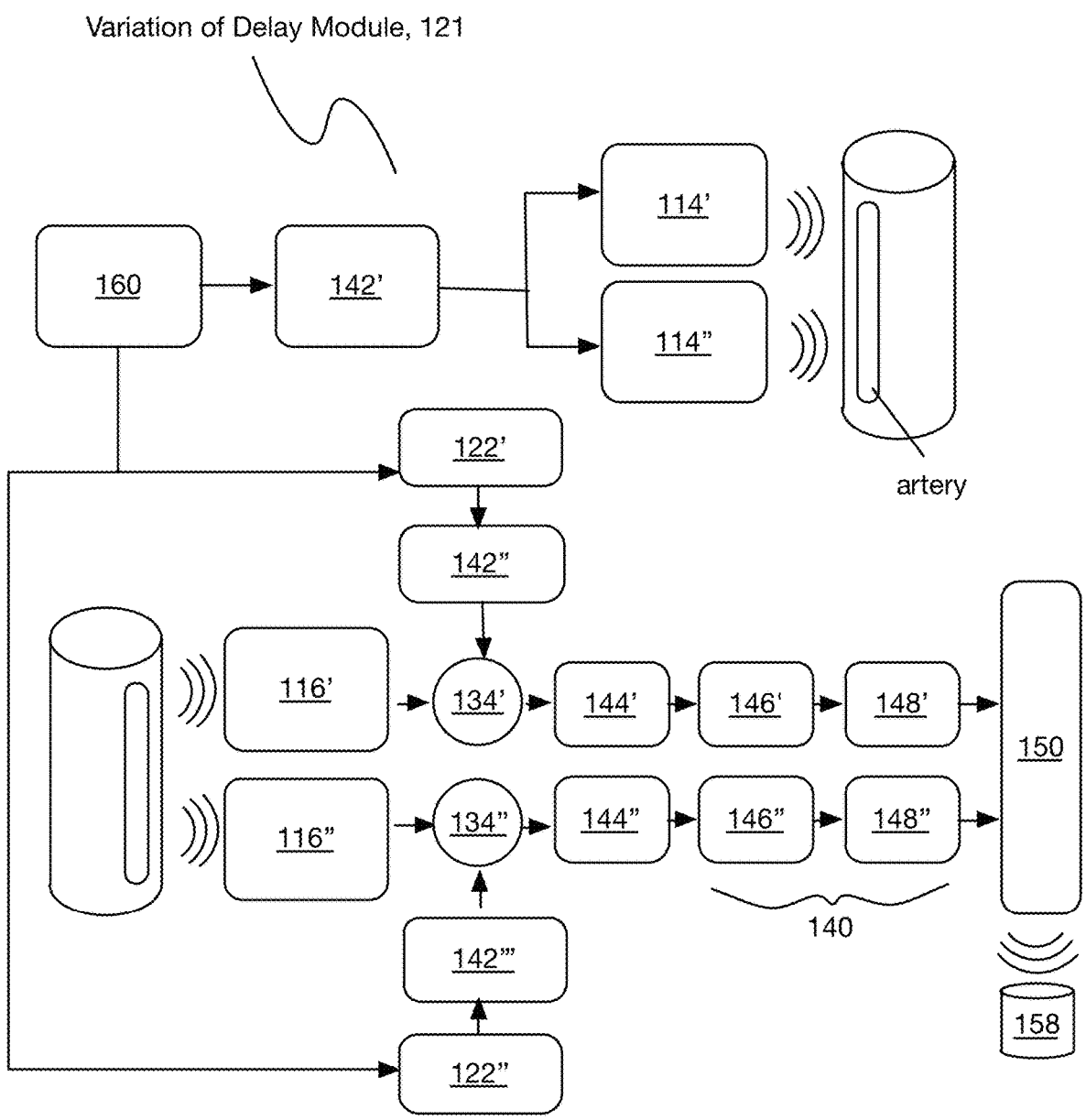

In a second variation, as shown in FIG. 6B, the delay module 121 can be a digital delay module 121 configured to perform digital delay on a signal dataset. In this variation, one or more pulse signals can be input into one more digital delay modules 121 (e.g., digital delay chip, fixed delay lines selectable by the processing and control subsystem). In a specific example, a first and a signal pulse signal dataset can be input into a first pulse shaper module 142' for subsequent transmission as incident signals. The first and second pulse signal datasets can be additionally or alternatively be input into a first and second delay components 122', 122", the output of which can be input into a second and a third pulse shaper module 142", 142"', respectively. The second and third pulse shaper modules 142", 142"' can be electrically coupled to a first and second mixing component 134' and 134", the output of which can be conditioned and processed for determining biometric measurement results. However, the digital delay modules 121 can be otherwise configured.

Figure 6C:
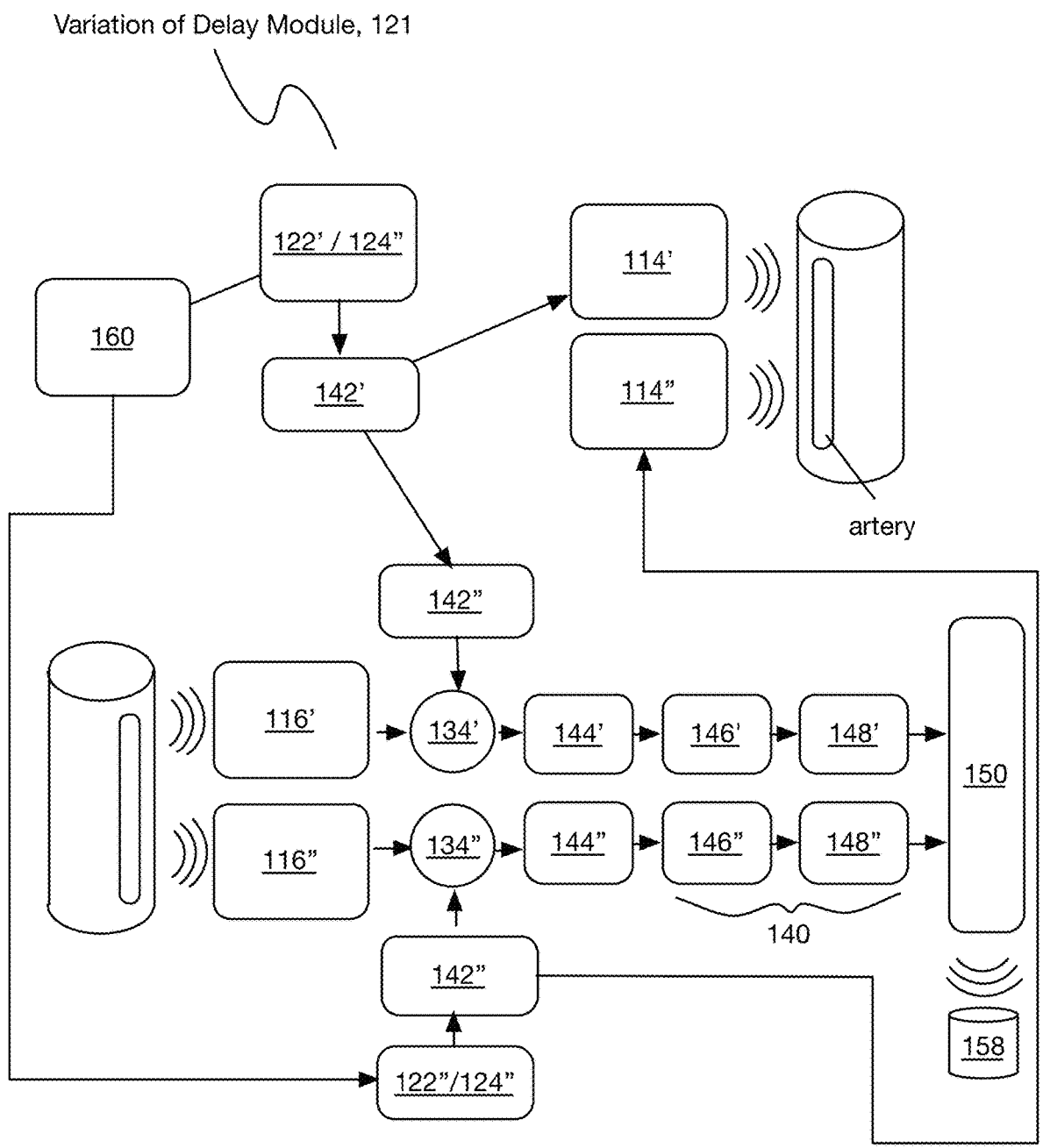

In a third variation, as shown in FIG. 6C, the delay module 121 include a switched fixed delay line module including one or more switches 124 and one or more a resistor-capacitor (RC) circuit paths characterized by a delay value (e.g., each RC circuit path defining a different delay value). The one or more switches 124 can selectively feed pulse signals (e.g., generated by the pulse signal generator 160) into one or more RC circuit paths. The processing and control system 150 can control the switch 124 with control and clock signals. However, the delay module(s) 121 can be configured in any suitable manner.

In any of these variations or other variations thereof, the delay module 121 can be configured to generate a first delayed pulse signal dataset from delaying a first pulse signal dataset with a first delay setting, and to generate a second delayed pulse signal dataset from delaying a second pulse signal dataset with a second delay setting. The pulse signals can include one or more: damped sinusoidal signals (e.g., from generating a pulse width modulated signal by a processing and control system 150 and passing the pulse width modulated signal through a pulse shaper module 142 including, for example, NAND gates and/or AND gates), a waveform generator chip-generated signal (e.g., periodic pulse signals, periodic sinusoid signals, periodic triangular phase signals, etc.), modified pulse width modulated signals (e.g., from generating a first and a second pulse wave modulated signal with the processing and control system 150, and feeding the pulse wave modulated signals into separate pulse shaper modules 142, etc.), and/or any other suitable signal. Pulse signal datasets can be the same, partially distinct, or fully distinct. Further, the first and the second delay settings can be the same or different. In examples where the delay module 121 is configured to delay datasets using multiple delay settings, the delay module 121 can include a plurality of components (e.g., digital potentiometers, delay circuits, etc.) configured to delay a pulse signal. For example, the delay module 121 can include a first delay component 122' (analog, digital, or delay line), as shown in FIGS. 6A, 6B, and 6C, which can be electrically coupled to and proximal a first mixing component 134' of the detector module 130, the first delay component 122' operable to generate a first delayed pulse signal dataset (e.g., from processing a first pulse signal dataset with a first delay setting), and a second delay component 122" electrically coupled to and proximal a second mixing component 134" of the detector module 130, the second delay component 122" operable to generate a second delayed pulse signal dataset (e.g., from processing a second pulse signal dataset with a second delay setting). In this example or another example, the delay module 121 can be operable between a first mode where the first delay component 122' outputs the first delayed pulse signal dataset based on the first delay setting determined based on processing a first preliminary pulse signal dataset collected at the first RF sensor device 110', and a second mode where the second delay component 122" outputs the second delayed pulse signal dataset based on the second delay setting independently determined based on processing a second preliminary pulse signal dataset collected at the second RF sensor device 110". However, any suitable number of signal datasets can be delayed by the delay module 121 using any number of delay settings and components.

Any number of delay modules 121 can additionally or alternatively be included in the RF system 105.

3.2.B Detector Module

The signal modification module 120 can include a detector module 130 functioning to detect change (e.g., phase, frequency, time delay, amplitude, etc.) between a reference signal and a reflected signal. The detector module 130 is preferably configured to generate a phase detected pulse signal dataset (e.g., with new amplitudes and/or frequencies), such as from mixing two or more pulse signals, but can additionally or alternatively generate any suitable detected signal dataset. The detector module 130 is preferably configured to mix a reflected pulse signal dataset (e.g., generated from an RF sensor device 110 from reflected pulse signals) and a delayed pulse signal dataset (e.g., generated from the delay module 121), but can mix any suitable signals. New amplitudes and/or frequencies produced by a detector module 130 can result from phase changes between signals input into the detector module 130, but can result from any suitable combination of phases and/or frequencies of the constituent signals (e.g., addition, difference, average, etc.). In more detail, motion of a blood vessel can result in a phase shift (e.g., periodic phase shift), which causes a signal amplitude to change. In examples, the amplitude across multiple radar pulses can be captured as representative of a blood pressure pulse wave. The detector module 130 can include any one or more of: passive mixers (e.g., including diodes), active mixers (e.g., including amplification devices), mixing components 134 integrated in an integrated circuit, discrete components, unbalanced mixers, single balanced mixers, double balanced mixers, switching mixers, phase locked loop and/or any suitable component for mixing signals.

The detector module 130 is preferably electrically coupled to a delay module 121 (e.g., for receiving a delayed signal dataset from the delay module 121). Further, the detector module 130 is preferably electrically coupled to an amplification module 144 configured to receive one or more phase detected pulse signal datasets. Additionally or alternatively the detector module 130 can be electrically coupled to a pulse shaper module 142 and/or any other suitable component for receiving/mixing pulse signal datasets.

In a variation, the detector module 130 can include a plurality of mixing components 134, each mixing component 134 operable to generate phase detected signal datasets (e.g., using different mixing parameters such as different operations applied to the frequencies of the constituent signals input into the mixing component 134, using similar mixing parameters, etc.). For example the detector module 130 can include a first and a second mixing component 134", where the first mixing component 134' is operable to generate the first phase detected pulse signal dataset (e.g., from mixing a first reflected pulse signal dataset with a first delayed pulse signal dataset), and where the second mixing component 134" is operable to generate a second phase detected pulse signal dataset (e.g., from mixing a second reflected pulse signal dataset with the second delayed pulse signal dataset).

Any number of detector modules 130 can additionally or alternatively be included in the RF system 105.

3.2.C Pulse Shaper Module

The signal modification module 120 can include a pulse shaper module 142 functioning to modulate pulse signals. The pulse shaper module 142 include any one or more of: a pulse width modulator, NAND gates, AND gates, ring modulator, plate modulator, Heising modulator, control grid modulator, clamp tude modulator, Doherty modulator, outphasing modulator, and/or other suitable signal modulation component. The signal modification module 120 is preferably operable to generate a modulated pulse signal dataset.

The signal modification module 120 is preferably electrically coupled to the RF sensor device 110 and/or a delay module 121. As such, incident signals transmitted by an RF sensor device 110 and/or the pulse signals delayed by the delay module 121 can be derived from the modulated pulse signal dataset. Additionally or alternatively, the signal modification module 120 can be electrically coupled to any suitable component (e.g., a processing and control system 150 that generates a pulse width modulated pulse signal dataset.

In a variation, the signal modification module 120 can include a pulse shaper module 142. The pulse shaper module 142 can be electrically coupled to a pulse signal generator 160, where the pulse shaper module 142 can be operable to generate a modulated pulse signal dataset derived from the set of pulse signals generated by the pulse signal generator 160. The pulse shaper module 142 preferably modulates a pulse signal dataset to define a an envelope shape (e.g., a damped sinusoidal envelope), but a pulse signal possessing any suitable envelope and/or other characteristics can be generated with the pulse signal generator 160 and/or the signal modification module 120. In an example, the signal modification module 120 can include a frequency modification module operable to dynamically adjust the frequency of a pulse signal envelope. The frequency optimization unit can dynamically tune the frequency of the envelope (e.g., damped sinusoidal envelope) to obtain a target received signal amplitude and/or to minimize signal noise. The frequency modification module can be implemented as hardware (e.g., retained in the housing 170 of the RF system 105), as software (e.g., executable by the processing and control system 150), disposed at a network connected device, and/or be implemented in any suitable form.

Any number of pulse shaper modules 142 can additionally or alternatively be included in the RF system 105. However, the signal modification module 120 can be configured in any other suitable manner.

3.2 Processing and Control System

The system 100 can include a processing and control system 150 communicably coupled to the signal modification module 120, the processing and control system 150 operable to generate a biometric measurement result for the user based on the modified reflected signal dataset. The processing and control system 150 functions to receive, process, and/or transmit signal data derived from a reflected signal dataset collected at an RF sensor device 110. The processing and control system 150 can additionally or alternatively function to control power provision, to control signal modification by the signal modification module 120, and/or perform any other suitable operation. The processing and control system 150 can additionally or alternatively include a processing subsystem 152, a communications module 154, a power module 156, and/or any other suitable component.

The processing and control system 150 can be fully and/or partially implemented as part of the RF system 105 (e.g., retained in a housing 170 of the RF system 105), with one or more remote servers, with a distinct user device (e.g., a user mobile phone 310, a laptop, a desktop, a tablet, a medical device, etc.), and/or in any suitable configuration.

The processing and control system 150 is preferably mounted to and/or integrated with the substrate 108 (e.g., printed circuit board), but can be alternatively distinct from a substrate 108. The processing and control system 150 can be positioned proximal a first edge of the substrate 108, and distanced a second opposing edge of the substrate 108 (e.g., where an RF sensor device 110 is proximal). Components of the processing and control system 150 can be integrated with one or more substrates 108, be distinct components, and/or possess any suitable form. For example, charging circuitry in power module 156 can be embodied in a separate printed circuit board or integrated into a main printed circuit board. However, the processing and control system 150 can possess any suitable geometry, orientation, location, construction materials, and/or any other suitable characteristic.

Further, the processing and control system 150 is preferably electrically coupled to other components (e.g., RF sensor devices 110, signal modification modules 120, pulse signal generators 160, conditioning modules 140, supplemental sensor modules 165, input modules 180, output modules 185, etc.), but can be otherwise related to components of the system. Components of the processing and control system 150 can be activated manually (e.g., by a user input at the input module 180), automatically (e.g., in response to satisfaction of a condition), continuously, periodically, externally (e.g., through external signaling from a remote server), and/or through any suitable means.

Any number of RF processing and control systems 150 can additionally or alternatively be included in the RF system 105. However, the processing and control system 150 can be configured in any suitable manner.

3.2.A Processing Subsystem

The processing and control system 150 can include a processing subsystem 152 functioning to control components of the RF system 105, determine parameters for operating components of the RF system 105, and/or process data collected and/or generated at the RF system 105. For example, signal data derived from received reflected signals collected at an RF sensor device 110 can be received by the processing subsystem 152 for processing. Data received by the processing subsystem 152 can be stored in memory 153 of the processing subsystem 152, stored in remote databases (e.g., in response to transmission by the communications module 154), displayed at an output module 185, stored and/or displayed at a distinct user device, encrypted, and/or otherwise processed. Data received and/or generated by a processing subsystem 152 can be stored and/or presented in association with a user identifier (e.g., name, digital identifier, username and password, biometric identifier, e-mail, etc.) and/or a user account.

The processing subsystem 152 is preferably operable between (e.g., can be operated in an individual mode, operated in multiple modes in parallel, in serial, etc.) a: control mode, a parameter determination mode, an output generation mode, and/or any other suitable mode. In a first variation, the processing subsystem 152 is operable in a control mode for controlling one or more components of the RF system 105. For example, the processing subsystem 152 can be operable in a control mode where the processing system controls the pulse signal generator 160 and the delay module 121.

Additionally or alternatively, the processing subsystem 152 can be operable in a parameter determination mode for determining one or more parameters (e.g., identifying initial parameters, updating parameters, optimizing parameters, etc.) according to which components of the RF system 105 (e.g., signal modification module 120) can be operated. For example, the processing subsystem 152 can be operable in a parameter determination mode where the processing system determines delay settings (e.g., to communicate to the delay module 121 for delaying pulse signal dataset). In a specific example, the processing system can be operable to determine a first delay setting based on a first preliminary pulse signal dataset collected at the first RF sensor device 110', and determine a second delay setting independently from determining the first delay setting, based on a second preliminary pulse signal dataset collected at the second RF sensor device 110". In another specific example, the processing system can be operable to determine a delay setting for modifying signal amplitude to be within a predetermined range of a target amplitude (e.g., defined based on an input range of an analog-to-digital converter module 148 of the RF system 105).

Additionally or alternatively, the processing subsystem 152 can be operable in a output generation mode for generating one or more outputs (e.g., pulse parameters, cardiovascular parameters, etc.). For example the processing system can be operable to generate a cardiovascular parameter based on a set of inputs including one or more: signal datasets derived from a reflected signal datasets, modified signal datasets (e.g., phase detected pulse signal datasets, delayed pulse signal datasets, modulated signal datasets, etc.), RF sensor device 110 parameters (e.g., distance between RF sensor devices 110, orientation of RF sensor devices 110), user parameters (e.g., skin thickness, target artery, body shape, body weight, demographic parameters, etc.), supplemental sensor data (e.g., motion sensor data, optical sensor data, etc.), and/or any other suitable parameters.

Any number of processing subsystems 152 can additionally or alternatively be included in the RF system 105. However, the processing subsystem 152 can be configured in any other suitable manner.

3.2.B Communications Module

The processing and control system 150 can include a communications module 154 functioning to receive and/or transmit signal-related data (e.g., signal datasets, pulse parameters, biometric measurement results such as cardiovascular parameters, etc.), control instructions (e.g., for controlling a component of the RF system 105), user-related data (e.g., user inputs, user preferences, user metadata, etc.), and/or any other suitable data. As such, the communications module 154 can function as a central biometric measurement hub with the capability to expand the scope of biometric measurements.

The communications module 154 can be any wired or wireless interface compatible for communication with network devices operable to establish communication between any components of the RF system 105, an information module, and/or any suitable component. The communications module 154 can include any one or more of Ethernet, USB, lightning connector 802.11, Bluetooth, ANT+, Zigbee, Z-wave, ultra-wideband (UWB), near-field communications (NFC), cellular, satellite, optical, and/or any other suitable wired and/or wireless technology. The communications module 154 can be be operable to transmit data in the form of a push notification, email, alert, tweet, text message, multimedia message, post, update, and/or any suitable form. The data transmission can be in real-time, near real-time, scheduled, in a batch, or piggybacked on other transmissions, and/or otherwise configured.

In a variation, the RF system 105 can be communicably coupled to a remote sensor and/or biometric measurement device through the communications module 154. In another variation, RF system 105 comprises of memory expansion slots such that additional memory module(s) can be added for biometric data storage. In another variation, communication between a distinct user device (e.g., a user mobile computing device) and the RF system 105 can be established through the communications module 154. In an example, the communications module 154 can include a Bluetooth wireless communications module 154 operable to exchange data and commands between the distinct user device and the RF system 105. Any number of communications modules 154 can additionally or alternatively be included in the RF system 105. However, the communications module 154 can be configured in any suitable manner.

3.2.C Power Module

The processing and control system 150 can include a power module 156 functioning to provide power to components of the RF system 105. The power module 156 can be a battery unit (e.g., rechargeable battery), capacitive storage unit, solar cells, energy scavenging unit or power module 156 for wired or wireless power transfer. Battery charging can be through USB, outlet, wireless charging, and/or other suitable means. In an example, charging could occur through other devices such as laptops or computers, or built-in charging units in furniture. In a variation, the power module 156 is nominally in a power efficiency mode that conserves power resources.

In another variation, the power module 156 can be operable in an active operation mode from a lower power mode (e.g., in response to launching of an application associated with the RF system 105, in response to detecting an indicator from the user regarding initiation of signal acquisition, etc.). The active operation mode can be achieved through wireless wakeup or switching power modes. The power module 156 can re-enter a low power mode in response to application termination, signal acquisition completion, and/or other suitable conditions. The power module 156 can enter a low power mode immediately upon a trigger event and/or a predetermined time after the trigger events. Any number of power modules 156 can additionally or alternatively be included in the RF system 105. However, the power module 156 can additionally or alternatively be configured in any suitable manner.

3.2.D Information Module

The processing and control system 150 can include an information module 158 functioning to store RF system 105-related data (e.g., signal-related data, control instructions, user-related data, etc.) and/or other suitable data. In a variation, RF-system related data can be synchronized between an information module 158, an RF system 105, and/or a distinct user device. In another variation, the information module 158 can be operable to transmit data in response to a pull (e.g. request for information). The information module 158 can include any one or more of: a remote server or a collection of servers, storage devices, or computing devices such as personal computer, mobile phone 310, home monitoring system, vehicular system, exercise equipment, or medical equipment, (e.g. bedside monitors, portable biometric monitoring devices, hospital patient monitors), and/or other suitable components located at any suitable location. Any number of information modules 158 can additionally or alternatively be included in the RF system 105. However, the information module 158 can be configured in any other suitable manner.

3.4 Pulse Signal Generator

Figure 8A:
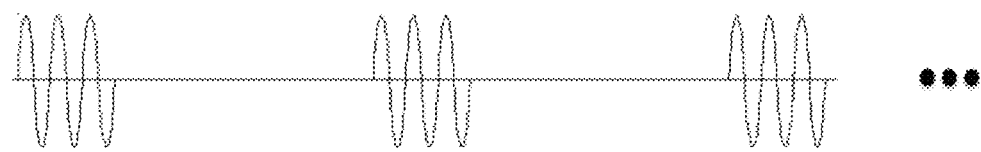
FIG. 8A-8B illustrate examples of waveforms generated by a signal generator in a variation of an embodiment of the system.
Figure 8B:
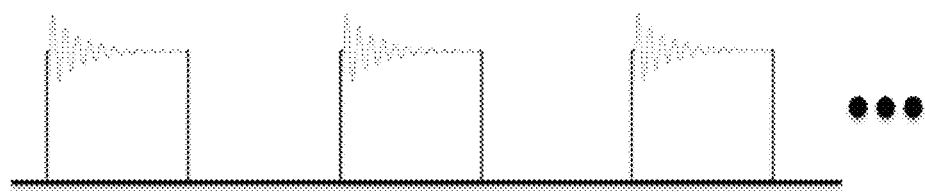

The system 100 can additionally or alternatively include a pulse signal generator 160 functioning to generate pules signals for transmission by an RF sensor device 110, for modification by a signal modification module 120, and/or for any other suitable purpose. The pulse signal generator 160 can include a processing subsystem 152 (e.g., which can also be used as a digital signal processing unit), but can optionally be distinct from the processing subsystem 152 used for signal processing. In an example, as shown in FIG. 8A, the pulse signal generator 160 can generate a waveform pulse signal. The generated pulse signals can be transmitted by one or more RF sensor device 110 continuously, periodically (e.g., at predetermined time intervals, at dynamically determined temporal indicators such as based on supplemental sensor data, etc.). In an example, as shown in FIG. 8A, the waveform pulse signal can include sinusoidal waveforms of fixed amplitude and duration, and/or any other suitable sinusoidal waveforms. In another example, as shown in FIG. 8B a periodic pulse wave with a damped sinusoidal signal as the pulse envelope. In this example, the pulse signal can possess a low frequency pulse wave of several MHz with a high frequency damped sinusoidal envelope of several hundred MHz. However, generated pulse signals can have any suitable pulse, sinusoids, period, phase, amplitude, frequency, and/or any suitable characteristic. Furthermore, any quantity of pulse signals can be generated. For example, the pulse signal generator 160 can generate a first pulse width modulated pulse signal for transmission by a first RF sensor device 110' (e.g., after modulation by a pulse modification module), and a second pulse width modulated pulse signal for transmission by a second RF sensor device 110".

The pulse signal generator 160 can be implemented in any one or more of: hardware (e.g., a waveform generator chip), software (e.g., executable by the processing and control subsystem), and/or any suitable form. The pulse signal generator 160 can be electrically coupled to the signal modification module 120 (e.g., a pulse shaper module 142), a delay module 121, an RF sensor device 110, a detector module 130, a pulse splitter module, and/or any other suitable component of the RF system 105. Any number of pulse signal generators 160 can additionally or alternatively be included in the RF system 105. However, the pulse signal generator 160 can be configured in any other suitable manner.

3.5 Conditioning Module

The system 100 can additionally or alternatively include a conditioning module 140 functioning to condition one or more signal datasets (e.g., a reflected signal dataset, a delayed signal dataset, a phase detected signal dataset, etc.) to generate a conditioned signal dataset for downstream processing by a processing and control system 150 in generating biometric measurement results (e.g., cardiovascular parameters). The conditioning module 140 can include any one or more of: an amplification module 144, a filtering module 146, a converter module 148 (e.g., analog-to-digital, digital-to-analog, etc.), a normalization module, a noise reduction module, a smoothing module, a model fitting module, a transformation module, and/or any other suitable conditioning module 140. Any component of the conditioning module 140 can be coupled to any other component of the conditioning module 140 (e.g., where the output of a component feeds into another component as an input) and/or component of the RF system 105. In examples, as shown in FIGS. 6A-6C, the RF system 105 can include an amplification module 144 electrically coupled to the detector module 130, and operable to generate an amplified pulse signal dataset from amplifying a signal dataset (e.g., phase detected signal dataset); a filtering module 146 electrically coupled to the amplification module 144, and operable to generate a filtered pulse signal dataset from filtering the amplified pulse signal dataset; an analog-to-digital converter module 148 electrically coupled to the filtering module 146, and operable to generate a digital pulse signal dataset from converting the filtered pulse signal dataset; and where the processing and control system 150 is operable in the output generation mode to generate a biometric measurement result based on the digital pulse signal dataset.

In another example, the output of a pulse signal generator 160 can be coupled to an amplification module 144, which can be coupled to a transmit antenna 114 (e.g., where pulse signals generated by the pulse signal generator 160 can be amplified, and subsequently transmitted to the transmit antenna 114 to be transmitted as incident signals). The output of amplifier 133 can additionally or alternatively be coupled to a delay module operable to delay the signals output by the amplification module 144.

In another example, the output of the detector module 130 can be coupled with a filtering module 146. The filtering module 146 can be operable to filter signals at unwanted frequencies in order to outputs signals in a desired frequency range. The output of a filtering module 146 can be coupled with an amplification module 144, and the resulting signal can be coupled with an analog to digital converter (ADC). In an example, the signal input into ADC 125 is a representation of the repetition frequency of the reflected signal. Any number of conditioning modules 140 can additionally or alternatively be included in the RF system 105. However, a conditioning module 140 can be otherwise configured.

3.6 Supplemental Sensor Module

The system 100 can additionally or alternatively include a supplemental sensor module 165 functioning to collect supplemental sensor datasets for use in generating biometric measurement results, dynamically initiating signal acquisition, and/or for any other suitable purpose.

The supplemental sensor module 165 can include any one or more of: motion sensors (e.g., accelerometers, gyroscopes, etc.), optical sensors (e.g., infrared light sensor, photosensor, LED light sensor for photoplethysmography, cameras, ambient light sensors, ultraviolet light sensors, etc.), bioelectrical signal sensors (e.g., ECG sensors, EEG, sensors, etc.), bioimpedance sensors (e.g., GSR sensors, EIT sensors), audio sensors (e.g., microphones), location sensors (e.g., GPS, magnetometers, proximity sensors), temperature sensors (e.g., humidity sensors, thermometers, ambient temperature sensor, etc.), barometers, biometric sensors (e.g., fingerprint sensor, nucleic acid analyzer, perspiration sensor, pulse oximeter, weight, blood analyzer), and/or any other suitable sensors.

The supplemental sensor module 165 is preferably communicably coupled to a processing system 150 (e.g., operable to receive and/or process supplemental sensor datasets, to generate and/or transmit control instructions to the supplemental sensor module 165 such as to initiate signal acquisition.

The supplemental sensor module 165 can be positioned proximal, distant, and/or at any suitable location an RF sensor device 110 and/or any other suitable component of the RF system 105. The supplemental sensor module 165 is preferably retained within a housing 170 of the RF system 105, but can additionally or alternatively be implemented fully or partially at a distinct user device (e.g., the supplemental sensor module 165 can include a motion sensor of a user's mobile phone 310). However, the supplemental sensor module 165 can be positioned at any suitable location.

The supplemental sensor module 165 can be operable to collect supplemental sensor data concurrently with an RF sensor device 110 collecting RF sensor datasets, but can additionally or alternatively be operable to collect supplemental sensor data independent of RF sensor device 110 signal acquisition, and/or at any suitable time. Any number of supplemental sensor modules 165 can additionally or alternatively be included in the RF system 105. However, the supplemental sensor module 165 can be configured in any suitable manner.

3.7 Housing

Figure 16:
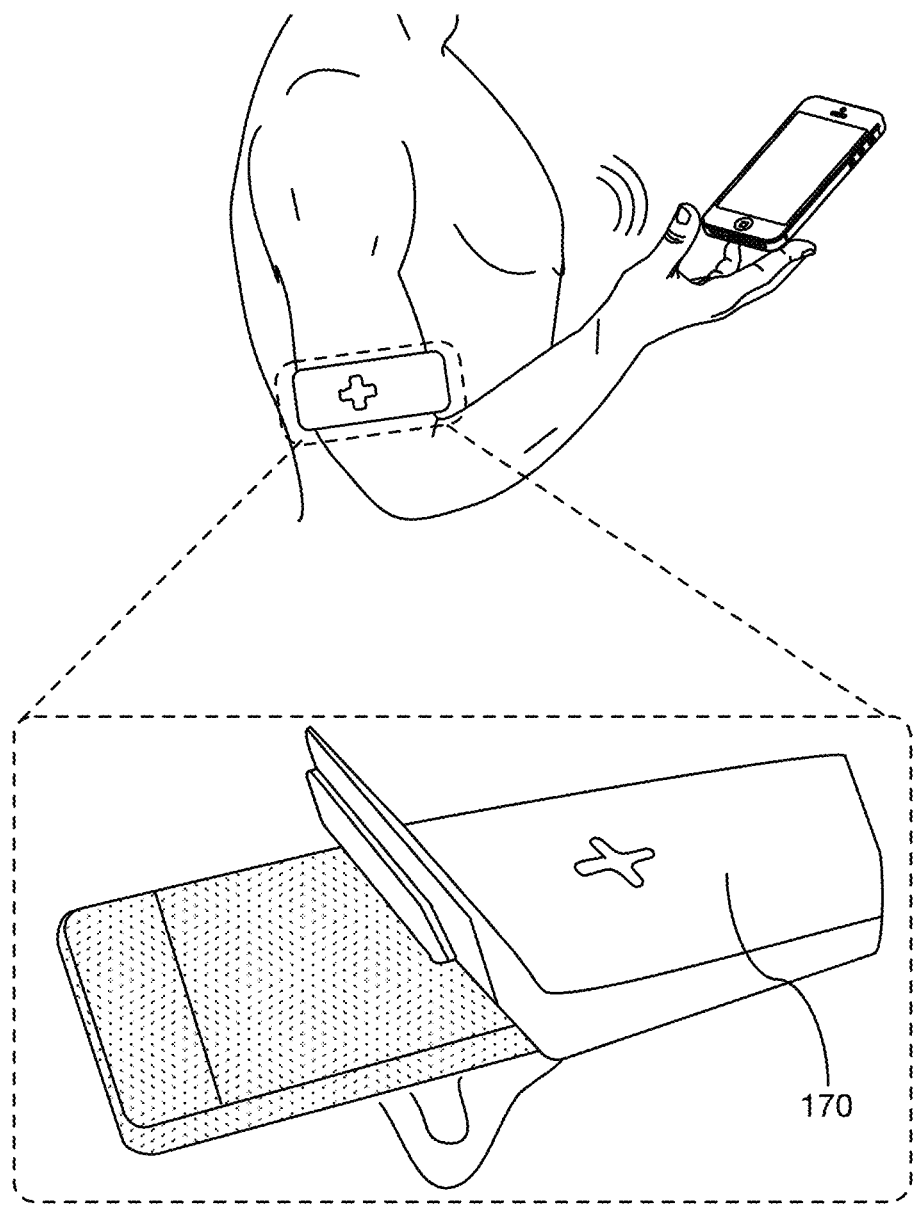
FIG. 16 is a schematic representation of a housing variation in an embodiment of a system.

As shown in FIG. 16, the system 100 can include one or more housings 170 retaining one or more other components of the RF system 105. The housing 170 functions to mechanically support and/or shield components of the RF system 105 (e.g., the RF sensor device 110, the signal modification module 120, components of the processing and control system 150, etc.). The housing 170 can additionally or alternatively include a band 172. The housing 170 preferably substantially enclose components of the RF system 105, but can additionally or alternatively partially enclose or not enclose components of the RF system 105.

As shown in FIGS. 15A-15D, the housing 170 can embody a card (e.g., rectangular prism) form factor. In examples, the housing 170 can define a front side, and opposing back side, a bottom side, a top side, and opposing side walls. In a specific example, the front side can define a output module region (e.g., at which an output module 185 can be positioned). In another example, a side wall can include an input module region (e.g., at which an input module 180 such as a button can be positioned). However, any suitable components can be positioned at and/or have any suitable positional relationship to regions of the housing 170.

One or more portions of the housing 170 can be substantially flexible, substantially rigid, and/or have any suitable rigidity level. For example, the housing 170 can include a flexible band 172 physically adaptable to the contour of an arm region of the user (e.g., proximal the brachial artery). In another example, the housing 170 can be substantially rigid and possess a rectangular form factor.

Figure 15A:
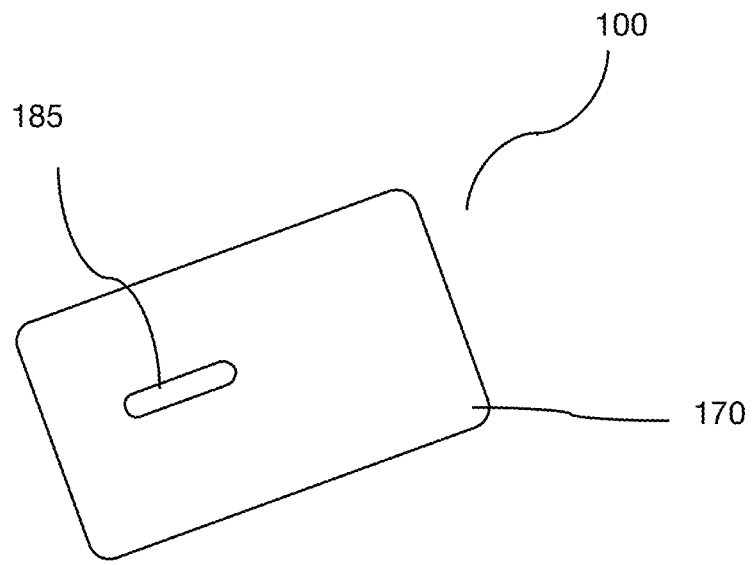
FIGS. 15A-15D are schematic representations of card form factor variations in an embodiment of a system.

The housing 170 is preferably substantially fluid impermeable, but can alternatively be permeable to fluid. The housing 170 can be constructed with materials including any one or more of: metals (steel, copper tungsten, aluminum, etc.), plastics (e.g., acrylonitrile butadiene styrene, etc.), glass (e.g., fiberglass, etc.), elastomers (e.g., silicone rubber), polymers, and/or any other suitable materials. In a specific example, as shown in FIGS. 15A and 15C, the housing 170 can be constructed with plastic parts forming the top and bottom sides of the housing 170, and a metal frame 70c disposed in between the top 70a and bottom 70b parts. The metal frame 70c can provides stiffness and/or structure to housing 170.

The housing 170 can additionally or alternatively include a coupling mechanism (e.g., coupling mechanisms associated with a band 172, and/or other support structure enabling the RF system 105 to be worn on the body and/or proximal the body of one or more users). Any number of housings 170 can additionally or alternatively be included in the RF system 105. However, the housing 170 can be configured in any suitable manner.

3.8 Input Module

Figure 15B:
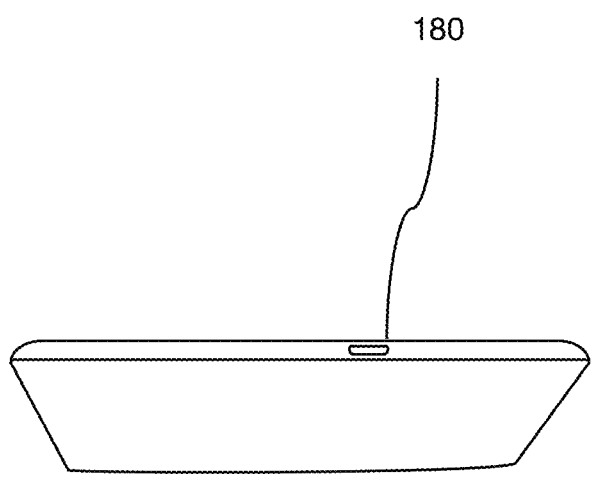
Figure 15C:
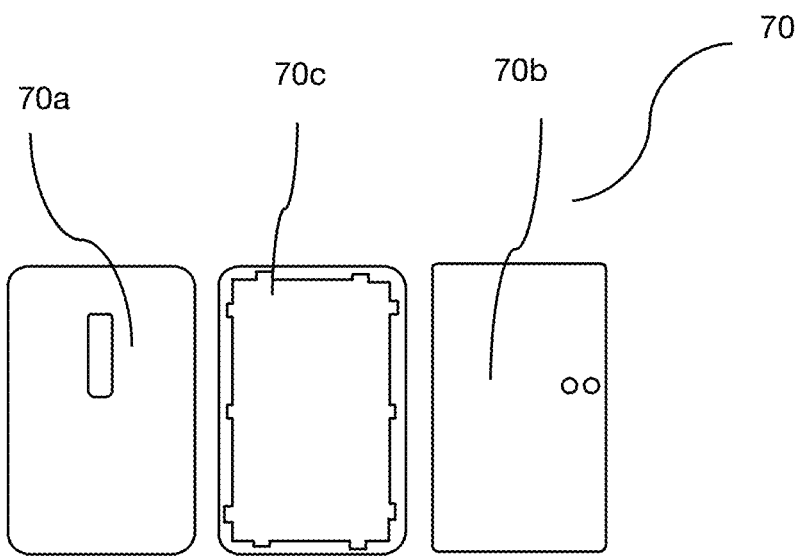
Figure 15D:
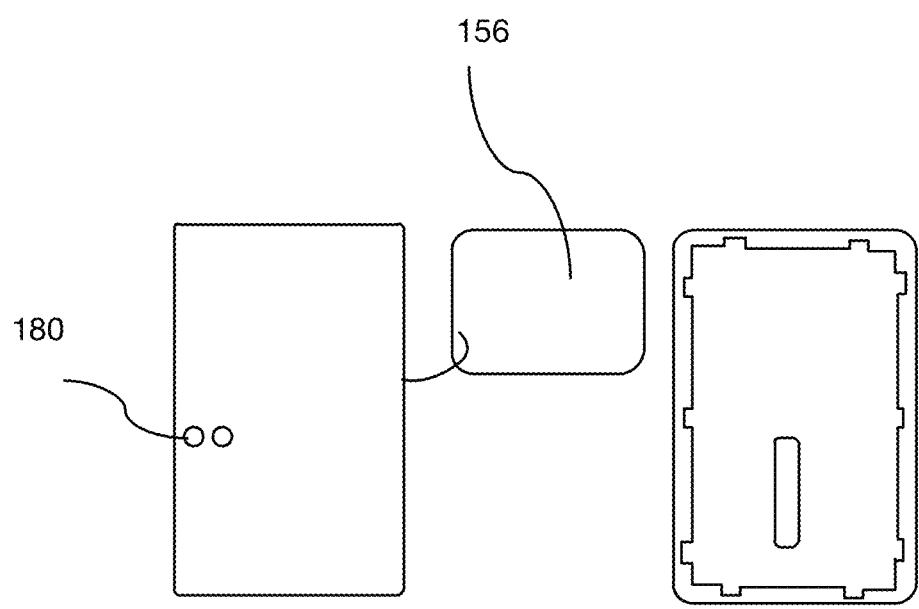

As shown in FIGS. 15B and 15D, the system 100 can additionally or alternatively include an input module 180 functioning to receive a user input for operating the RF system 105. The input module can be positioned at any one or more of: the RF system 105, a distinct user device (e.g., a paired mobile phone 310, a paired smart watch, a medical device, a laptop, etc.). User inputs can include any one or more of: commands to select a software application, initiate biometric data collection, terminate biometric data collection, initiate data analysis, interact with biometric measurement results, schedule a care provider appointment, contact a care provider, communicate biometric measurement results to an individual, and/or perform any other suitable action. For example, the input module 180 can be operable to receive a user input indicating subject profile information such as age, gender, weight, exercise frequency, past medical history, income level, education level, personal habits (e.g. smoker, drinker, etc.), etc. Such information can be used in biometric measurement result computations and/or interpretations. Input module 180 can include any one or more of: a button, switch, dial, touch screen, keyboard, touchpad, microphone, trackball, gesture recognition unit, gaze tracking unit, remote control interface operable to interface with an external remote controller, and/or any other suitable input means.

In an example, the input module 180 is a button operable to be pressed by a user to initiate signal acquisition (e.g., by an RF sensor device 110, by a supplemental sensor module 165, etc.), and corresponding biometric measurement results (e.g., cardiovascular parameters) can be presented at the output module 185 (e.g., displayed on the display unit). The button can also be used to enable other functions, such as displaying measurement history, battery power level, date, time, among others, based on timing of click, number of clicks, duration of click, among others.

Any number of input modules 180 can additionally or alternatively be included in the RF system 105. However the input module 180 can be configured in any suitable manner.

3.9 Output Module

The system 100 can additionally or alternatively include an output module 185 functioning to present RF system 105-related data to one or more entities (e.g., a user, a care provider, a family member, etc.). The output module 185 can include any one or more of: a haptic feedback module, an audio feedback module, a visual feedback module such as a display or projector, and/or any suitable type of feedback module. The display can include any one or more of: LCD, LED, organic LED, electronic paper, and/or any suitable components. Organic LEDs can include any one or more of: a passive matrix, active matrix, transparent, top-emitting, foldable, white, etc.). The output module 185 can be operable to present notifications (e.g., to initiate signal acquisition, to perform other actions, etc.) to the user. Notifications can be presented based on timers, satisfaction of conditions (e.g., lack of signal acquisition for a predetermined period of time), and/or based on any suitable criteria. The output module can be included with the RF system 105, a distinct user device (e.g., smart watch, mobile phone 310, laptop, desktop computer, medical device, etc.). Any number of output modules 185 can additionally or alternatively be included in the RF system 105. However, the output module 185 can be configured in any other suitable manner.

3.10 Additional or Alternative Variations

Figure 9:
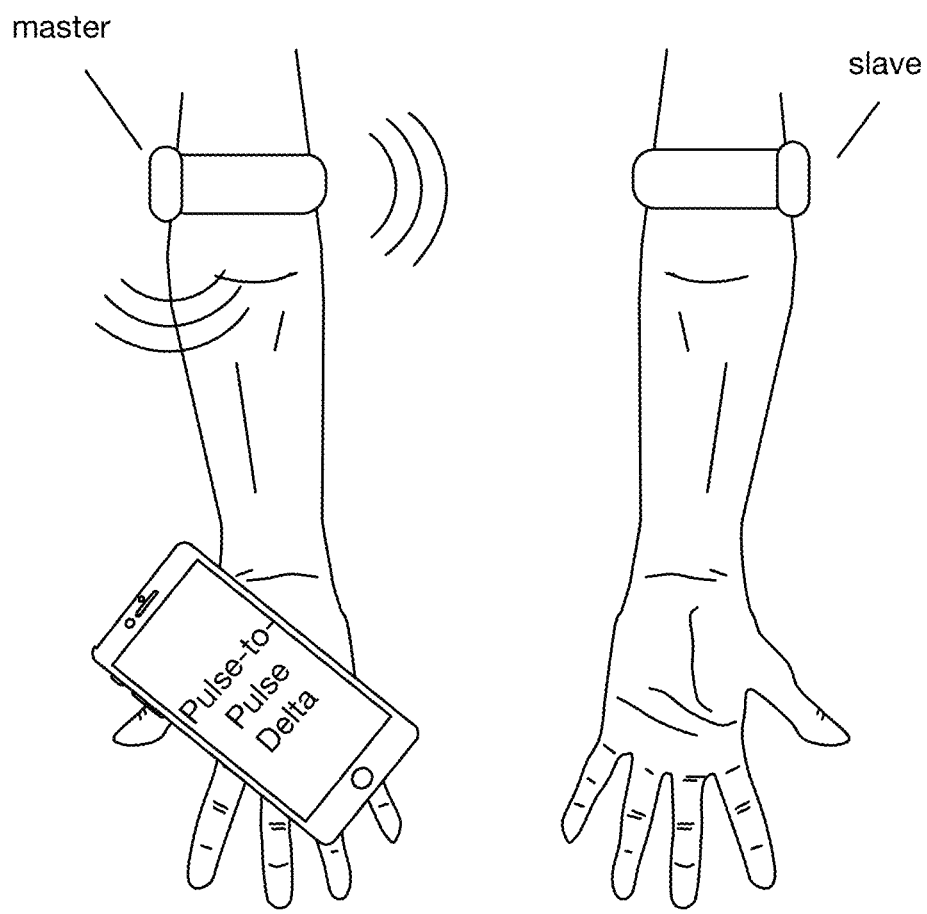
FIG. 9 is a schematic representation of a multi-radio frequency system variation in an embodiment of a system.
Figure 10:
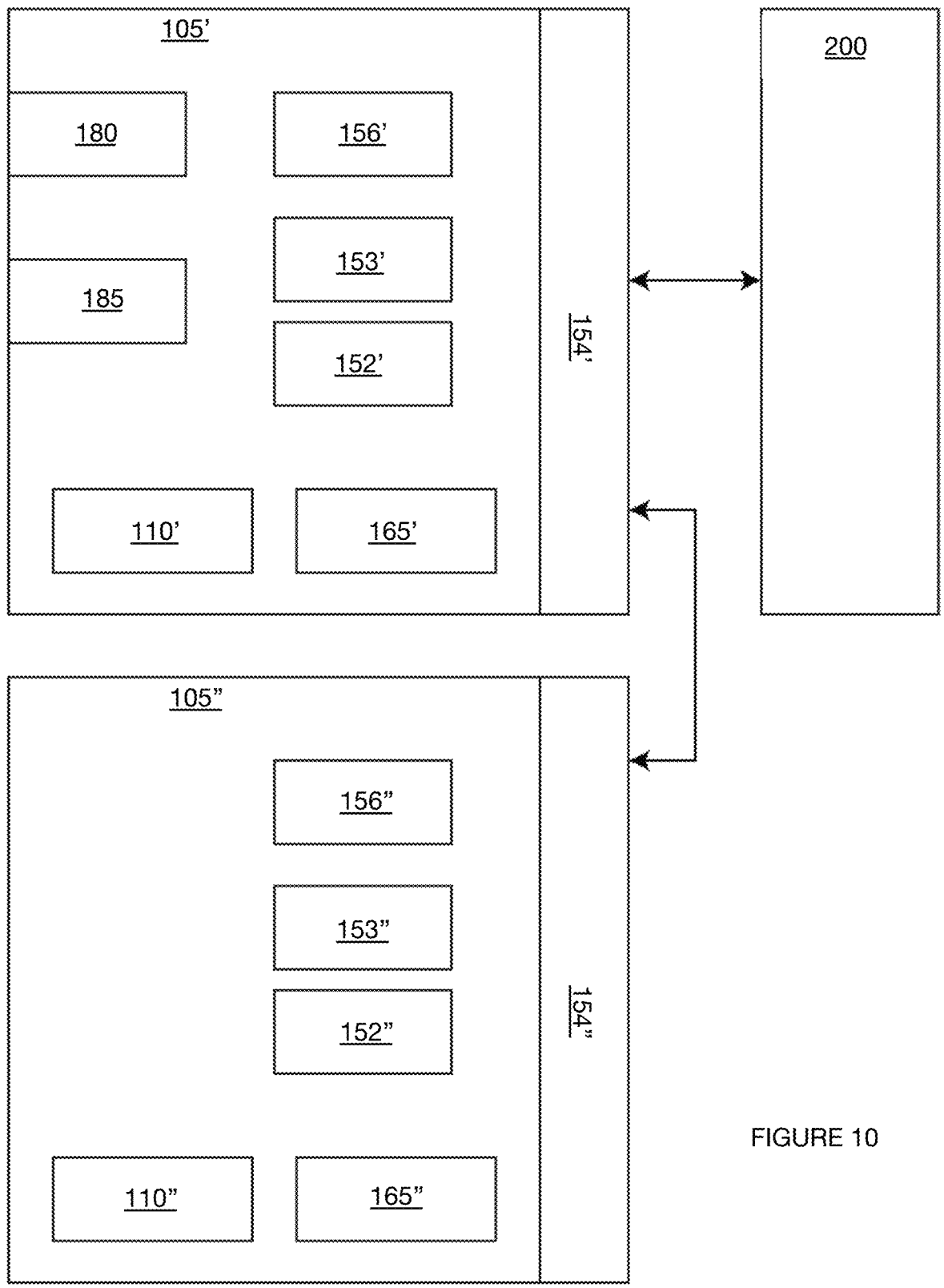
FIG. 10 is a schematic representation of a multi-radio frequency system variation in an embodiment of a system.

In a variation, as shown in FIGS. 9-10, the system 100 can include a plurality of RF systems 105', 105". The RF systems 105 are preferably communicably coupled (e.g., through wired means, wireless means, in real-time, in batch based on a configurable condition, etc.), but can alternatively be communicable independent (e.g., where each RF system 105 is communicably coupled to a distinct user device and/or information module 158 but communicably independent from each other). The RF systems 105 can operate dependently or independently from each other. In an example, a user can wear and/or position two RF systems 105 on opposing arm regions (e.g., opposing wrists).

In a specific example, the system 100 can include a first RF system 105' including a first and second RF sensor device 110', 110" (e.g., where the first and second RF sensor device 110', 110" are included in a first RF sensor device module); and a second RF system 105" including a third and a fourth RF sensor device 110', 110" (e.g., where the first and second RF sensor device 110', 110" are included in a second RF sensor device module.). The first RF sensor device module can be operable to generate a first reflected signal dataset, and each RF sensor device of the first RF sensor module can be operable in a receiving mode wherein the RF sensor device receives signals reflected from first incident signals proximal a first artery of the user, the first incident signals derived from the set of signals. The second RF sensor device module can be operable to generate a second reflected signal dataset, and each RF sensor device of the second RF sensor module can be operable in a receiving mode wherein the RF sensor device receives signals reflected from second incident signals proximal a second artery of the user, the second incident signals derived from the set of signals. In this or another specific example, a processing and control system 150 (e.g., of the first RF system 105', of the second RF system 105", distinct from the RF systems 105, etc.) can be operable in an output generation mode to generate a cardiovascular parameter based on a plurality of cardiovascular parameters (e.g., differences in blood pressure parameters) derived from a plurality of pulse signal datasets (e.g., a first reflected pulse signal dataset derived from the first RF system 105', and a second reflected pulse signal dataset derived from the second RF system 105"). Differences in blood pressure parameters taken on the left arm versus the right arm can be correlated with congenital heart disease, aortic dissection, peripheral vascular disease, unilateral neuromuscular abnormalities, and a risk of future cardiovascular conditions.

Figure 12:
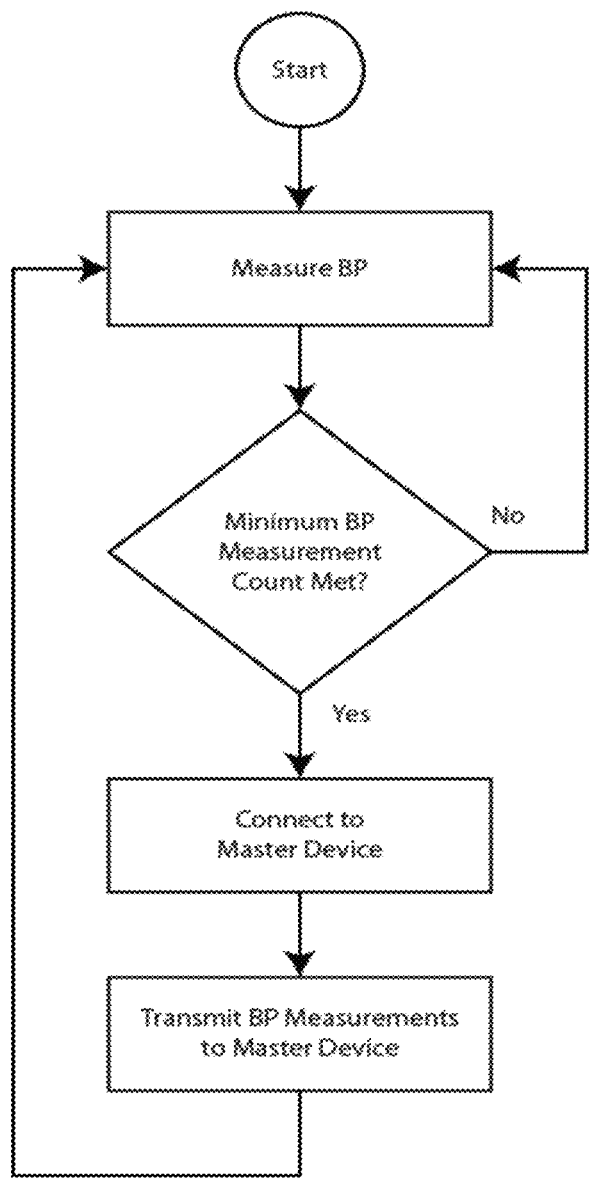
FIG. 12 is a processing flow chart of a multi-radio frequency system variation in an embodiment of a system.

In a variation, as shown in FIGS. 9-10, an RF system 105 can be configured as a master device and one or more other RF systems 105 can be configured as slave devices. For example, the system can include a first RF system 105' operable as a master RF system 105 and including a processing and control system 150; and a second RF system 105" operable as a slave RF system 105, the second RF system 105" including a wireless communications module 154 communicably coupled to the processing and control system 150 and operable between a receiving mode where the wireless communications module 154 receives control instructions from the master RF system 105, and a transmission mode where the wireless communications module 154 transmits second RF system 105" data (e.g., derived from a reflected pulse signal dataset collected at the second RF system 105") to the processing and control system 150. In an example, as shown in FIG. 10, a slave device can include fewer circuitry components (e.g., excluding an output module 185) compared to the master device. In examples, a plurality of RF system 105 can operate independently, in collaboration, and/or as part of a master/slave network. The master device can be operable to consolidate signal-related data retrieved from itself and/or from any slave devices, to perform data analysis, and/or to output cardiovascular parameters. In an example, as shown in FIG. 12, the slave device can be operable to process raw signal data collected at one or more RF sensor devices 110 and/or other sensor modules of the slave RF system 105, and/or to transmit the processed data (e.g., in real-time, in batch, etc.) to the master device.

Figure 11:
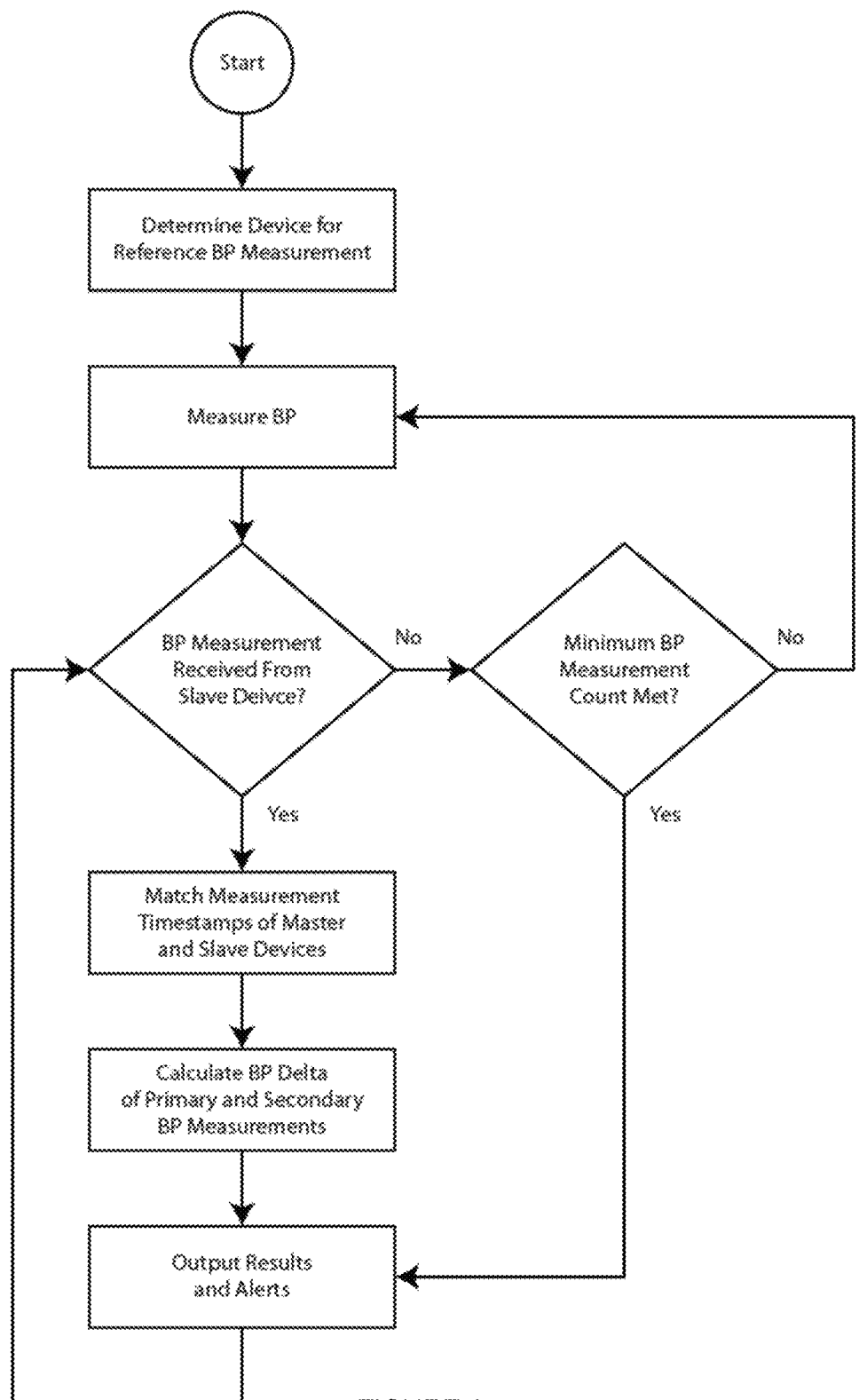
FIG. 11 is a processing flow chart of a multi-radio frequency system variation in an embodiment of a system.

In another variation, as shown in FIG. 11, an RF system 105 can be operable as a reference device (e.g., for generating reference signal datasets used in generating reference cardiovascular parameters). The reference device can be assigned manually by a user to a specific body location and/or the processing and control system 150 can be operable to automatically assign a device as the reference device. In an example, the arm that has the higher blood pressure reading over time can be considered to be the reference arm. In an example, automatic reference device assignment is based on current and/or historical biometric results at different body locations. For example, the reference device can be assigned based on a target arm that consistently measures higher blood pressure compared to the opposing arm. The reference device can be a master device, a slave device, a and/or any other suitable device. A user can specify that the master device be worn on a specific arm (i.e. left). Additionally or alternatively, a mater and a slave device can be labeled (e.g., at the housing 170, displayed at the output module 185, etc.) right or left to indicate the appropriate arm, a software application can indicate to the user which arm to wear which device, and/or other indicator mechanisms can be employed.

In this variation, cardiovascular parameters can be generated in association with each arterial pulse of the user. Cardiovascular parameters and/or associated signal datasets from a plurality of RF systems 105 can be correlated for generating a pulse-to-pulse delta (e.g., differences between cardiovascular parameters determined for different physiological locations such as the opposing arms). In an example, the devices on both arms are synchronized in time and each signal dataset is timestamped in order to generate a beat-to-beat comparisons between the two RF systems 105. Alternatively, time synchronization can be omitted. In an example, time reference signals (e.g., indicating a temporal indicator associated with a dataset) can be transmitted concurrently with the signal data. The device receiving the signal can examine determine a time offset between the signal datasets from distinct RF systems 105. The time offset can be used to align datasets (e.g., signal measurements, output parameters such as pulse parameters and/or cardiovascular parameters).

In examples, the pulse-to-pulse delta can be defined as a difference between the systolic and diastolic blood pressure parameters between the RF systems 105. The delta can be calculated as an average from a reference device, a group of devices treated as a reference group, or pair-wise among a group. In an example, the system can include a first and second RF system 105" operable to collect RF sensor device 110 data at opposing arms, and a third RF system 105 operable to collect RF sensor device data at a central artery of the chest. In this example, a delta between central and peripheral blood pressure can be calculated. In another example, a set of RF systems 105 can be operable at the arms, legs, and central artery simultaneously.

Signal-related data from any one or more of: a reference device, a non-reference device, a master device, a slave device, and/or any suitable RF system 105 can be output to the user (e.g., at the output module 185). When reporting blood pressure values from both arms, the value taken from the reference arm can be indicated as such. The difference in blood pressure readings between the two arms can be output to the user and an alert can be provided if the difference exceeds a threshold. In an example, a reference guide containing information about blood pressure and blood pressure difference between arms can be provided to the user on the output module 185.

Figure 13:
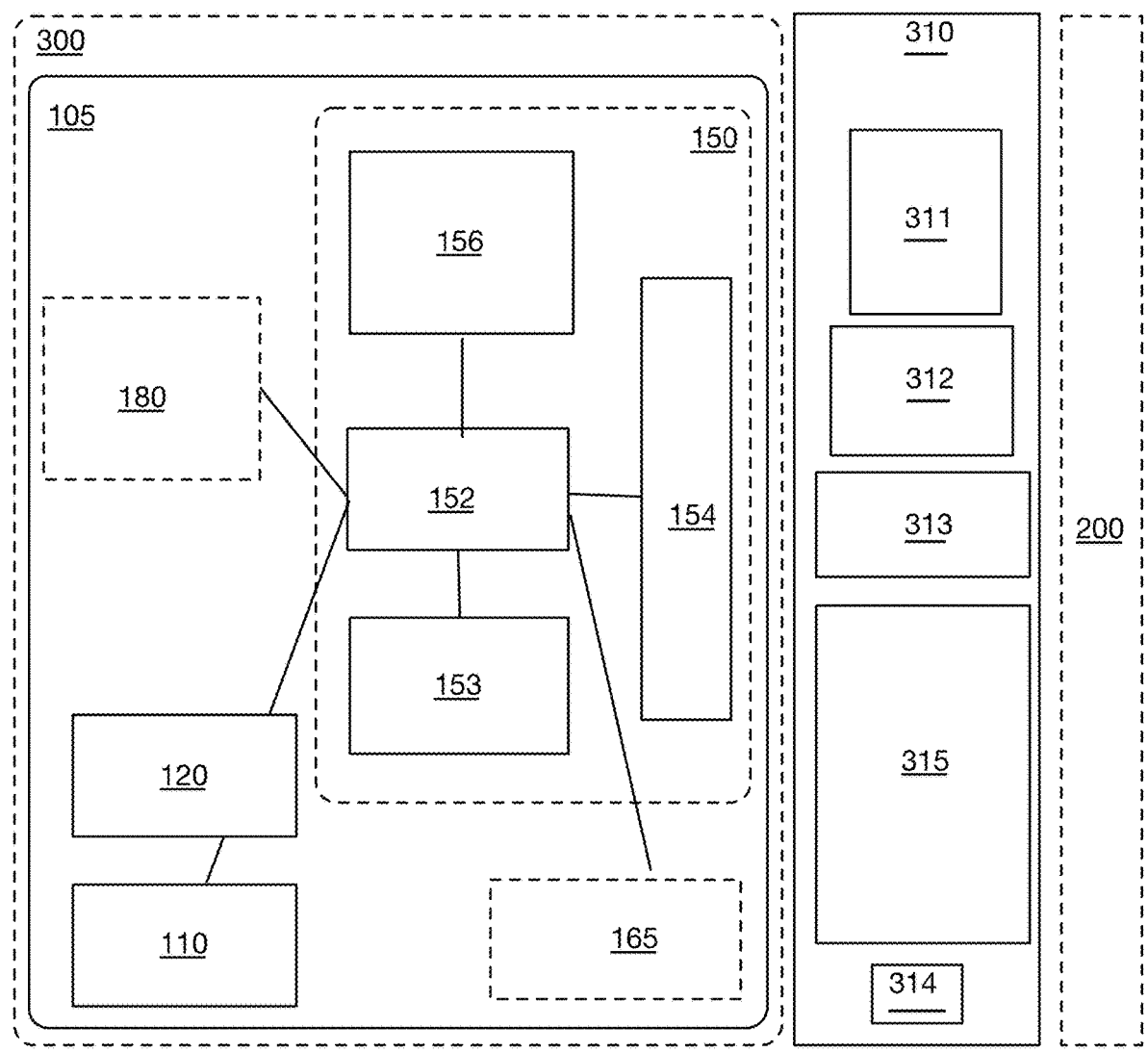
FIG. 13 is a schematic representation of a variation of an embodiment of a system.

In another variation, an RF system 105 can be a standalone apparatus, as shown in FIG. 1. For example, the RF system 105 can be a standalone wearable device. In another variation, the components in an RF system 105 and/or multiple RF systems 105 can be divided among multiple apparatuses with wired and/or wireless communication means interconnecting the multiple apparatuses. For example, a subset or all of input modules 180 and/or output module 185 can be disposed on a device physically separated from an RF system 105. In another example, an RF system 105 can be plugged into another electronic device for operation. In an example, the RF system 105 can be integrated within another electronic device, such as a mobile phone 310, tablet, watch, medical devices, or exercise equipment, among others. Any one or any combination of sensing, power, communication, processing, storage, input, output and other functionalities can be shared between an RF system 105 and the other electronic devices. In an example, as shown in FIG. 13, an RF system 105 can be embedded or integrated into a case 300 for an electronic device, such as a mobile phone 310. In another example, the RF system 105 can be disposed in and/or integrated into indoor and/or outdoor environments (e.g., table, chair, bed, wall, home monitoring system, vehicle). Hence, an RF system 105 can take on a variety of form factors, including, but not limited to, card, tag, box, watch, bracelet, ring, pendant, anklet, belt, clip, strap, clothing, earpiece, headset, glasses, phone, patch, e-skin helmet, monitoring system, medical equipment, or exercise machine, among others.

Figure 14A:
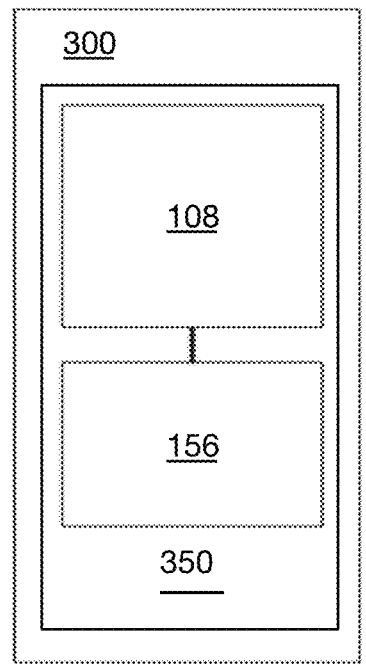
FIGS. 14A-14D are schematic representations of variations of mobile phone case implementations in an embodiment of a system

In another variation, an RF system 105 can be disposed on any surface via glue, clip, magnet, sticker, tape, Velcro™, screw, pocket, slot, tension, suction, or by embedding some or all of the circuitry inside the material making up the surface, among others. In one variation, the RF system 105 can be integrated into or disposed on a casing, covers, housings 170, straps, belts, or other structures used in conjunction with electronic devices (e.g. watch, mobile phone 310, tablet, laptop, medical device, computer, vehicle computer). In an example, as shown in FIG. 14A, a substrate 108 of the RF system 105 and a power module 156 are disposed on a component that is configured to be housed within a mobile phone case 300. In other examples, an RF system 105 can be disposed on the back of the mobile phone 310, on the inside surface 352a of the mobile phone case 300, and/or on the back surface of the mobile case 300.

In another variation, the RF system 105 can include an indicator indicating a location of itself relative to the surface it is disposed. The indicator can be in the form of markings indicating orientation and/or distance relative to one or more sides of the surface. In an example, an indicator can be located anywhere on a surface. In another example, a mobile phone case 300 (or surface RF system 105 is disposed upon) provides indication (e.g. markings, grooves, text, etc.) as to the optimal orientation and/or location of RF system 105. In an example, an application on mobile phone 310 provides indication to the user as to the proper orientation and/or location of RF system 105, possibly after determining the model and/or dimensions of the mobile phone 310, as shown in FIG. 4. In an example, mobile phone 310 determines the location and/or orientation of RF system 105 based on transmitted the RF signal profile, heat profile, accelerometer and gyrometer readings based on movement (e.g. vibration) of mobile phone 310, and/or digital image possibly captured by the mobile phone's 310 camera. For example, a digital photograph of RF system 105 disposed on a mobile phone case or back cover of mobile phone 310 can be analyzed (e.g. object recognition) by software on mobile phone 310. The analysis can indicate relative location and orientation of RF system 105 and/or components such as antenna 112 134, as shown in FIG. 4. This information can then used to provide an indication to a user for the optimal measurement position. In an example, processing subsystem 152 or mobile phone 310 determines whether or not a target is positioned properly based on sensor measurement values and/or analysis results. If the position of the target is incorrect or suboptimal, an output via output module 185 and/or software on mobile phone 310 provides feedback to the user guiding the subject to move the target location to a more optimal position. While this description is for mobile phones, other electronic devices can be substituted without changing the spirit of the invention.

Figure 14B:
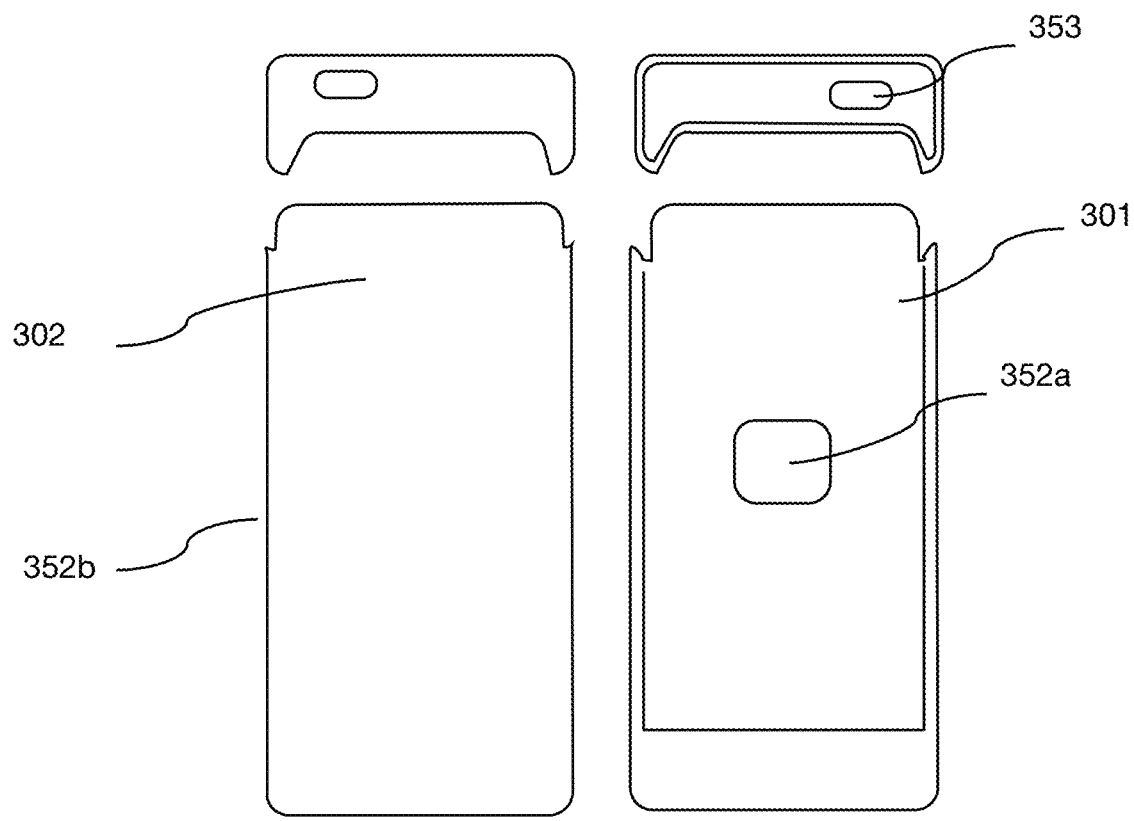
Figure 14C:
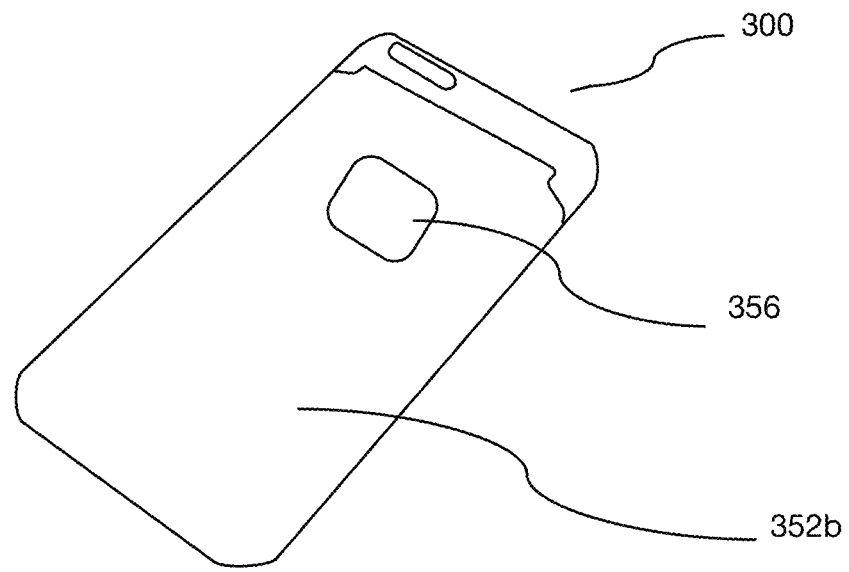
Figure 14D:
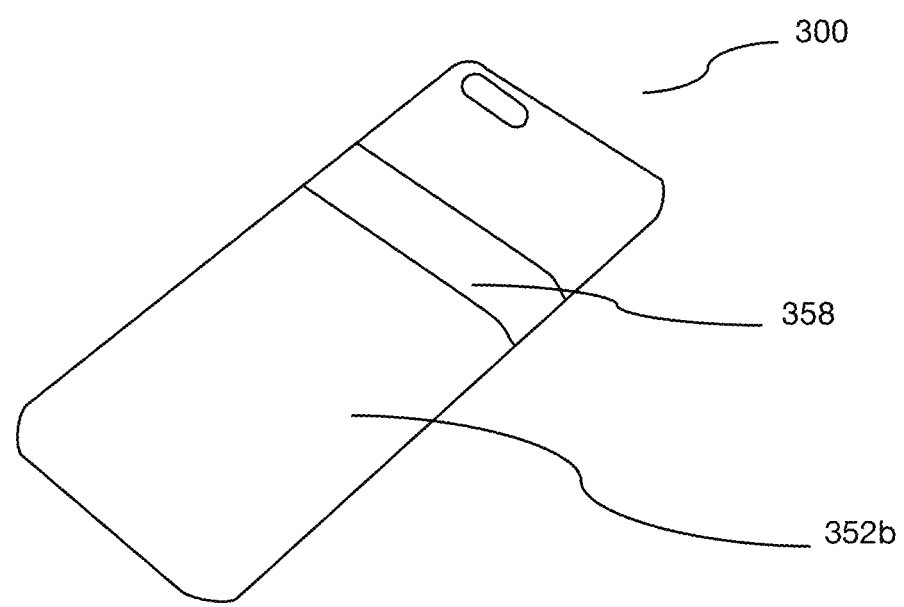

Similarly, the following description uses mobile phone case as an example, but can be applied to structures used in conjunction with other electronic devices. For example, FIG. 14A shows an example of RF system 105 components disposed on a mobile phone case 300. In other examples, case 300 is the back cover of a mobile phone. In an example, as shown in FIG. 2B, case 300 can include two pieces 301 and 302. The RF system 105 can be positioned on component 350 and/or fastened in piece 301. The other piece, 302, is laid on 301 such that RF system 105 can be sandwiched between 301 and 302, thereby securely positioned in case 300. In an example, RF system 105 has an input module 180 in the form of a button. The button can be used to activate RF system 105, reset RF system 105, or for other input functions. Such a button can be accessible to a user through the case 300 on the back exterior surface 352b or accessible on the inside of case 300. While the example described provides a button as an example, any other suitable other input means can be substituted. In another example, case 300 includes an input module 180 and an output module 185 such that a user interacts with RF system 105 and receives output on case 300. In an example, the back 352b of case 300 has an indented region 356 to aid the user in the proper positioning of the case relative to a subject's target (e.g. radial artery near a wrist), as shown in FIG. 14C. In another example, the back 352b of case 300 has markings 358 to aid the user in the proper positioning of the case for biometric measurements, as shown in FIG. 14D. The markings 358 can be printed text or diagrams, tactile indications (e.g. embossed dots, braille, indented grooves) or indications with a different color, material, or finish. In an example, the dimension of case 300 is designed to form a fit with mobile phone 310. In another example, a region in the front of case 300 is designed to form a fit with mobile phone 310. In another example, case 300 is a folio type of case whereby mobile phone 310 is on one side of the case while RF system 105, or components of RF system 105 are situated on the other side of the case. In an example, case 300 includes three or more pieces. Two of the pieces 301, 302 form a secure sandwiching of RF biometric RF system 105 as mentioned before and shown in FIG. 14B. The third piece 353 is slid on and off from the other two pieces 301, 302. Mobile phone 310 also slides into the other two pieces 301, 302. Once mobile phone 310 is inserted into the case 300, the third piece 353 is inserted onto the other two pieces 301, 302. In another example, the circuitry of RF system 105 is disposed on a flexible substrate material 350, thereby allowing flexible integration into a case 300 of any shape and/or size. In general, RF system 105 disposed on flexible substrate material 350 can be a stand-alone device fashioned in different shapes (e.g. bracelet) or shaped according to integration areas in other devices. In an example, case 300 comprises of shock absorbing material and/or protective structure around at least one surface of RF system 105 to provide drop or impact protection. In an example, case 300 comprises connector ports (e.g. USB, lightening connector) to interconnect external sensor and/or biometric measurement device(s) to RF system 105. This enables RF system 105 to act as a central biometric measurement hub with the capability to expand the scope of biometric measurements. In another example, case 300 comprises of memory expansion slots such that additional memory module(s) can be added for biometric data storage. In an example, case 300 comprises access to RF system 105 such that RF system 105 can be physically reset, diagnosed, or replaced. In an example, successive generations of RF system 105 are designed such that they can fit into the same case 300. This allows RF system 105 to be upgraded without changing the case.

As shown in FIG. 4, the RF system 105 can be operable to be positioned by a user holding a mobile phone 310 near an artery (e.g., radial artery) in the arm. Alternatively, mobile phone 310 can lean against a radial artery. As shown in FIG. 4, the display 312 on mobile phone 310 can displays an image, animation, or video to show proper positioning of case 300 relative to the target area of the subject. For example, an image shows an arm/wrist 52/53 on display 312 which visually indicates to a subject where to position his/her arm/wrist. For certain applications, such as blood pressure monitoring, the optimal antenna 112 position 60 is on top of the radial artery above the wrist. The case 300 is positioned on the inside of the arm 52 (palm facing up) and the antenna 112 is aligned to the top (thumb-side) of the arm 52. In an example, an application on mobile phone 310 determines what model of case 300 is being used and/or what phone the application is running on. The determination can comprise reading identifying information such as case ID or model number stored in memory 153 via the communications module 154. The application can then determines where the visual indicators should be positioned on the phone display based on the determination of the phone identifying information.

Figure 3:
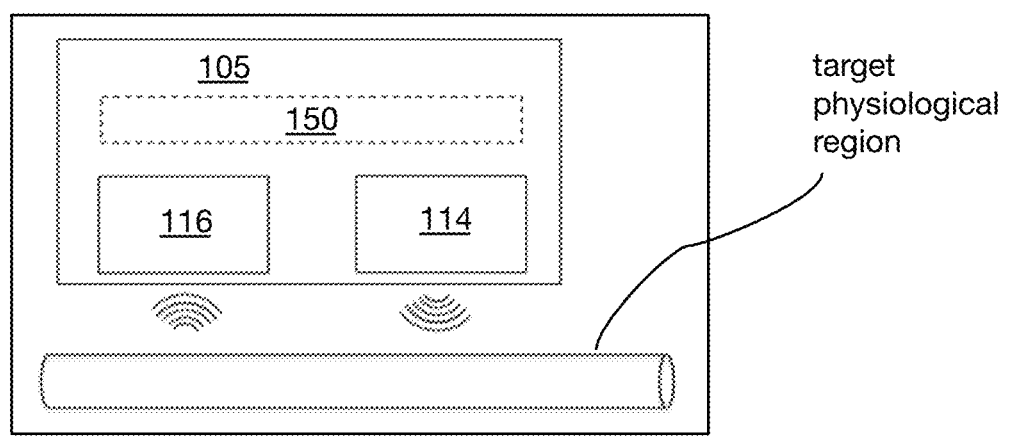
FIG. 3 is a schematic representation of outputted biometric measurement results in a variation of an embodiment of a system.

In an example, as shown in FIG. 3, RF system 105 can include a subset of RF system 105 components. For example, RF system 105 can exclude an output module 185, and a subset of other supplemental sensor module 165 (e.g. GPS). In this case, a user can activate the RF system 105 via a software application 314 and the input module 311 on the mobile phone 310. The software application 314 and components of mobile phone's 310 hardware control RF system 105 to collect biometric data using the RF biometric sensor 101. In this example, RF system 105 processes and analyzes the signal data and sends the results to mobile phone 310 (e.g., at a mobile device communications module 315) for display to the user via output module 312. For example, heart rate and/or systolic and diastolic blood pressure reading are generated based on biometric data collected using the RF biometric sensor 101 and are displayed on a touchscreen 312 on mobile phone 310. FIG. 3A shows the biometric measurement results displayed on mobile phone 310. Other information can also be displayed (e.g. progress, battery level, time, subject etc.). In another example, mobile phone 310 gathers sensing data from RF system 105, and possibly sensing data from itself to perform some or all signal processing and analysis to generate measurement results. In another example, mobile phone 310 gathers sensing data from sensors and/or from networked devices in addition to sensing data or measurement results from the RF biometric sensor 101 to generate contextual information and/or improve the accuracy of the biometric measurement result. One of skill in the art would understand that other functional divisions between RF system 105 and mobile phone 310 are possible. In an example, RF system 105 is activated manually through input means such as, but not limited to, button, tap, or gesture. In an example, under control of the software application 314, the measurement results are transmitted by mobile phone 310 to information module 158 via mobile phone 310. In another example, RF system 105 transmits the measurement results to information module 158 without first transmitting the results to mobile phone 310.

In another variation, the RF system 105 can be a part of a smart environment with interoperability with other sensors in the environment. For example, a smart environment can be a smart home or smart vehicle (e.g. car, boat, bus, plane). In an example, biometric measurement results can be classified into several classes. For example, the classes can be normal, worsening, or critical. A list of contacts (e.g. friends, family, caretaker, nurse, doctor, insurance agency) can be notified when measurements fall under worsening and/or critical. Emergency personnel can be notified when measurements fall under critical. When measurements fall under certain classes such as worsening or critical, RF system 105 and/or other device in communication contact with RF system 105 can be operated to capture location, video, audio, picture, text or other data and sent to predetermined entities. RF system 105 can be a part of an existing wireless network such as ZigBee, Z-wave, WiFi, or other local area network. The network can or can not have a centralized controller. If there is a centralized controller, RF system 105 can send an alert command to the controller in response to detecting a critical condition. The controller can control other sensors and/or actuators to respond to the alert. In an example, data from RF system 105 can be the basis for operating a door lock such that others can get in a house, a room or a vehicle when a critical condition is detected. The controller can command a door lock to open when authorized personnel wishes to gain access to the house, room or vehicle. In another example, the controller can command a door lock to open immediately. In an example, the presence or proximity of RF system 105 can be used to indicate whether or not a subject has left the house, room, or vehicle. If the subject is no longer present, the controller can command the lock to be locked. Similarly, biometric measurements from RF system 105 can be a basis for turning on/off lights (e.g. turning on porch light for emergency workers), thermostat, stove, fridge, and any other sensor/actuator devices in the environment. Biometric measurements from RF system 105 can be the basis of putting other sensors/actuators into predetermined operational states (e.g. activating hazard light in vehicle, activating vehicle braking, putting vehicle in self-operating mode, blinking porch light to notify passersby or neighbours, safely stopping exercise equipment). If the network does not have a controller, the RF system 105 can send alert information to other sensors/actuators directly or via other network nodes. In an example, biometric measurements from RF system 105 can indicate that a subject is exercising, sleeping, or in other states. Such indications can be used to put other sensors/actuators and/or electronic devices into preconfigured settings. For example, if a subject is sleeping, electronic devices can be put into do not disturb mode. Thermometer settings can be adjusted. On the other hand, if a subject is exercising, the thermometer setting can be lowered.

In an example, an alert from RF system 105 indicating critical condition can be sent to nearby vehicles or roadside connected vehicle infrastructure. Such alert can put nearby vehicles into emergency response mode (e.g. slow down, stop, move away) or influence traffic light control to prevent collisions.

In another variation, the RF system 105 can be a part of a smart body environment with interoperability with other wearable or embedded sensors or actuators. For example, a measured high blood pressure condition can be used to trigger automatic dispensing of medication, for example, through a wearable patch. In another example, RF system 105 can send alert signal to other user (e.g. doctors, emergency personnel) to remotely operate an on-body device to dispense medication, activate implanted defibrillator or other implanted devices. In another example, upon receiving alert, other users can connect with the subject via telephone, computer or teleconferencing to provide instructions to the subject or local care provider.

In an example, RF system 105 provides alert to a user if it is not being worn or if the device is not being worn by the right person. The determination can be achieved via biometric measurements and statistics.

In an example, RF system 105 can be in communication contact with a medicine dispenser. When measured biometric result exceeds a predetermined threshold, the medicine dispenser can alert the user (e.g. vibrate, audio) to take medication. The medicine dispenser can in addition dispense the appropriate amount and type of medicine based on the biometric results. However, the system 100 and/or components of the system 100 can be configured in any suitable manner.

4. Method

Figure 17:
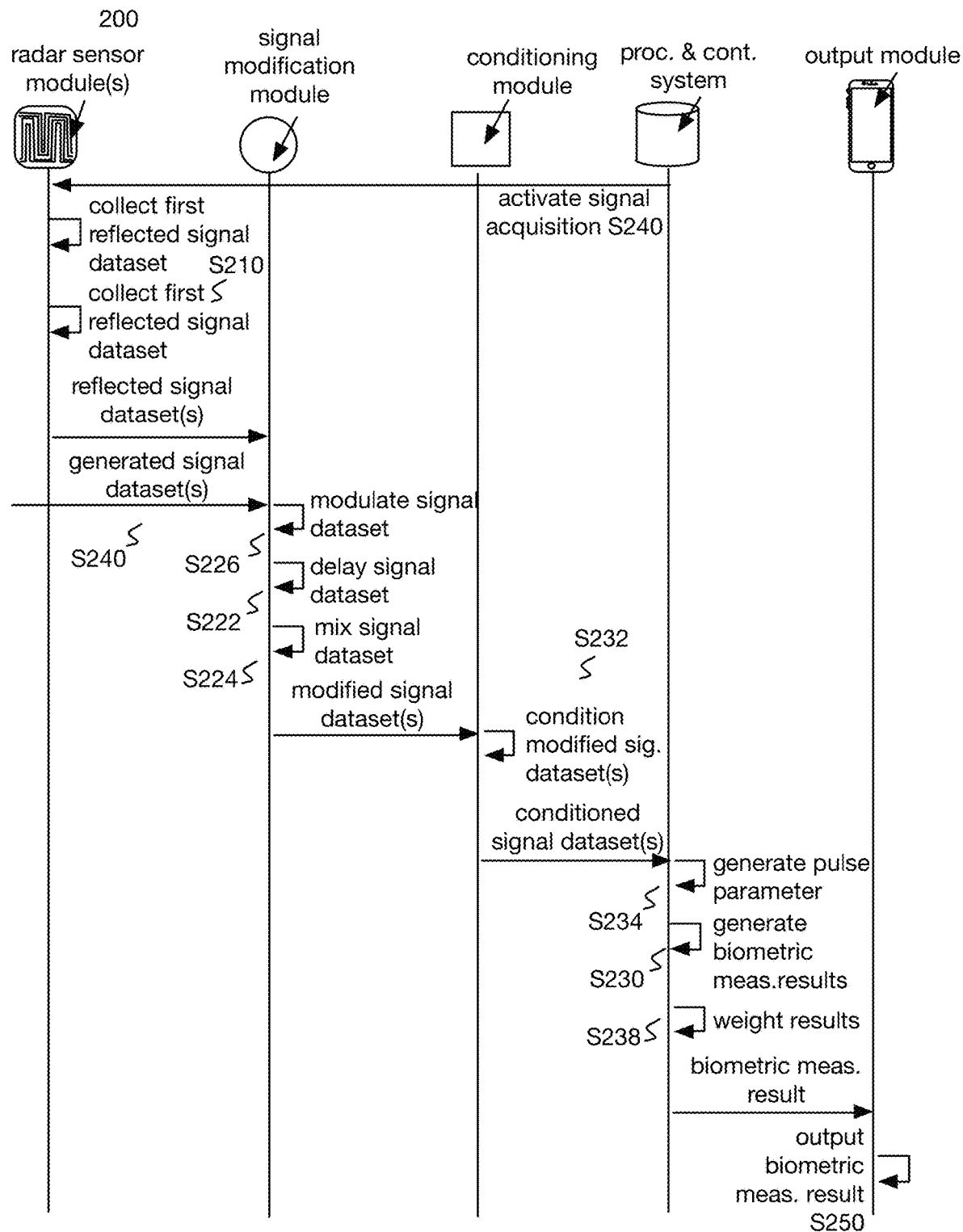
FIG. 17 is a flow chart representation of a variation of an embodiment of a method.

As shown in FIG. 17, an embodiment of a method for evaluating cardiovascular-related health of a user includes: collecting a reflected pulse signal dataset including pulse signals reflected in response to pulse signal transmission by an RF system towards an artery of the user S210; generating a modified pulse signal dataset based on modifying the reflected pulse signal dataset S220; and generating one or more biometric measurement results based on one or more pulse parameters derived from the modified pulse signal dataset, the biometric measurement result indicating the health of the user S230. Generating the one or more biometric measurement results can additionally or alternatively include: conditioning one or more pulse signal datasets (e.g., a reflected pulse signal dataset) S232, generating one or more pulse parameters describing pulse signals derived from the reflected pulse signal dataset S234, filtering signal-related data outliers S236, and/or weighting signal-related data S238.

The method can additionally or alternatively include: controlling signal acquisition operation S240, and/or outputting RF system-related information to the user S250.

In a variation, a method for evaluating cardiovascular-related health of a user includes: at each of a first and a second RF sensor device of an RF system, collecting a reflected pulse signal dataset including pulse signals reflected in response to pulse signal transmission by the RF system towards an artery of the user; at a delay module of the RF system, generating a delayed pulse signal dataset based on delaying a pulse signal dataset with a delay setting for modifying pulse signal amplitude to be within a predetermined range of a target signal amplitude; in response to collecting the reflected pulse signal dataset and generating the delayed pulse signal dataset, mixing the reflected pulse signal dataset and the delayed pulse signal dataset, thereby generating a phase detected pulse signal dataset; generating an amplitude-adjusted pulse signal dataset within the predetermined range of the target signal amplitude, based on conditioning the phase detected pulse signal dataset; determining a pulse parameter based on the amplitude-adjusted pulse signal dataset, the pulse parameter describing arterial motion of the artery; and determining a cardiovascular parameter based on the pulse parameter, the cardiovascular parameter indicating the cardiovascular-related health of the user.

The method functions to use a single- and/or multi-RF-based approach to non-invasively determining one or more biometric measurement results (e.g., cardiovascular parameters) describing the cardiovascular-related health of one or more users. The method can additionally or alternatively function to improve signal quality of signals collected by the RF system, such as through processing collected pulse signals into a suitable form for generating accurate biometric measurement results based on the modified pulse signals.

The method is preferably implemented by the system described above, but can be partially or fully implemented by a distinct user device (e.g., mobile phone, laptop, tablet, desktop, etc.) and/or any suitable device capable of deriving biometric measurement results from signal datasets collected by RF systems.

4.1 Collecting a Reflected Pulse Signal Dataset.

As shown in FIG. 17, Block S210 recites: collecting a reflected pulse signal dataset including pulse signals reflected in response to pulse signal transmission by an RF system towards an artery of the user. Block S210 functions to collect reflected pulse signals derived from incident signals transmitted towards a physiological region of the user, for downstream processing in generating biometric measurement results.

The reflected signal dataset preferably includes signals reflected by the target physiological region of the user, but can include any suitable reflected signals (e.g., signals reflected by clothing, by proximal objects, etc.). The reflected signal dataset is preferably includes reflected pulse signals but can additionally or alternatively include continuous wave, substantially continuous, discrete, pulse signals, other wave signals and/or any suitable signal types.

Collecting a reflected pules signal dataset is preferably in response to transmission of incident signals by one or more RF sensor devices of one or more RF system. Reflected signal data from a plurality of RF sensor devices and/or RF systems can be aggregated into a single reflected pulse signal dataset (e.g., by the processing and control subsystem, by a processor of an RF sensor device, etc.), multiple reflected pulse signal datasets, and/or otherwise combined or compartmentalized.

In a variation, the method can include collecting one or more reflected pulse signal datasets at a plurality of RF sensor devices. For example, the method can include collecting a first reflected pulse signal dataset at a first RF sensor device, and collecting a second reflected pulse signal dataset at a second RF sensor device (e.g., positioned at a known distance from the first RF sensor device). In this example, the first reflected pulse signal dataset can include pulse signals reflected in response to pulse signal transmission by a transmitter block of the first RF sensor device, and the second reflected pulse signal dataset can include pulse signals reflected in response to pulse signal transmission by a transmitter block of the second RF sensor device.

In this variation, the method can include concurrently collecting reflected signal datasets at a plurality of RF sensor devices, each reflected pulse signal dataset associated with a single time period. Additionally or alternatively, collecting reflected signal datasets at different RF sensor devices can be performed substantially concurrently, in serial, and/or at any suitable time in relation to each other. Collecting the reflected signal datasets can include generating an aggregate reflected signal dataset based on combining one or more reflected signal datasets (e.g., averaging, summing, normalizing, subtracting values, etc.) corresponding to a same time period, where the method can include modifying the aggregate reflected signal dataset at the signal modification module.

In this variation, the method can include transmitting a reflected pulse signal dataset from a first RF sensor device to a second sensor module (e.g., that is communicably coupled to the processing and control subsystem, where a single RF sensor device is directly electrically coupled to the processing and control subsystem).

Collecting a reflected pulse signal dataset is preferably performed at a receiver block (e.g., including one or more receive antennas), where the pulse signals are reflected in response to transmission of incident signals by a transmitter block (e.g. including one or more transmit antennas). However, any suitable component can collected reflected pulse signal datasets.

Collecting a reflected pulse signal dataset is preferably performed after transmission of incident signals by a transmitter block, but can be performed substantially concurrently with signal transmission (e.g., updating the dataset as reflected pulse signals are collected by one or more receiver blocks), and/or at any suitable time. The reflected signal dataset and/or individual reflected signal data of the dataset can be associated with a temporal indicator (e.g., time point, time duration, time period, etc.) indicating when the signals were collected at the RF sensor device, when the corresponding incident signals were transmitted, and/or indicating any other suitable event.

Collecting a reflected pulse signal dataset can additionally or alternatively include providing one or more RF systems operable to collect RF sensor device signal data at one or more physiological regions of the user. Target physiological regions preferably include arteries (e.g., proximal the arm, wrist, chest, etc.), but can additionally or alternatively include the aorta, veins, and/or any suitable physiological region exhibiting movement. Providing the RF system can include providing one or more standalone RF systems, RF systems integrated with a distinct user device (e.g., a user mobile phone, a user mobile phone case), and/or RF systems in any suitable form. However, providing one or more RF systems can be performed in any suitable manner.

Figure 19A:
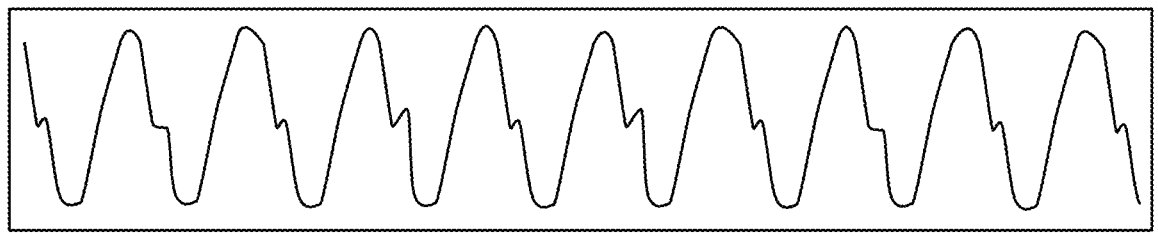
FIGS. 19A-19C respectively illustrate examples of a normal pulse signal, a saturated pulse signal, and a weak pulse signal in variations of an embodiment of a method.

Collecting a reflected pulse signal dataset can additionally or alternatively include generating one or more signals (e.g., pulse signals as shown in FIG. 19A) with a signal generator (e.g., pulse signal generator) of the RF system. Generated pulse signals can be used for transmitting incident signals (e.g., with an RF sensor device), modifying signal datasets (e.g., used as a constituent signal for mixing signals derived from the generated pulse signals with signals derived from reflected signal datasets), and/or for any suitable purpose. However, generating one or more signals can be performed in any suitable manner.

Collecting a reflected pulse signal dataset can additionally or alternatively include transmitting incident signals (e.g., generated as in Block S210, modified as in Block S220, etc.) towards a target physiological region. Transmitting incident signals is preferably performed with one or more transmit antennas (e.g., forming a transmitter block), but can be performed by any suitable entity. Transmitting incident signals can be performed by any suitable number of RF sensor devices and/or RF systems. However, transmitting incident signals can be performed in any suitable manner. However, collecting a reflected signal dataset can be performed in any other suitable manner.

4.2 Generating a Modified Signal Dataset.

As shown in FIG. 17, Block S220 recites: generating a modified pulse signal dataset based on modifying the reflected pulse signal dataset. Block S220 functions to modify signal data collected by one or more RF sensor devices to improve signal quality for determining biometric measurement results.

Generating a modified signal dataset can additionally or alternatively include: generating a delayed pulse signal dataset, generating a phase detected pulse signal dataset, generating a modulated pulse signal dataset, and/or any suitable operation. Block S220 can include generating a modified signal dataset from one or more of a: reflected signal dataset, generated signal dataset (e.g., from a signal generator), a different modified signal dataset, and/or any suitable signal dataset.

Generating a modified signal dataset is preferably performed at one or more of a: a delay module, a detector module, and/or a pulse shaper module, as described above, but can additionally or alternatively be performed at the processing and control system and/or any other suitable component. Generating a modified signal dataset is preferably performed subsequent to collecting a reflected signal dataset at an RF sensor device, but can additionally or alternatively be performed concurrently (e.g., modifying first collected reflected signal data while concurrently collecting new reflected signal data) and/or at any suitable time. However, generating a modified signal dataset can be performed at any suitable time.

4.2.A Generating a Delayed Pulse Signal Dataset

Figure 19B:
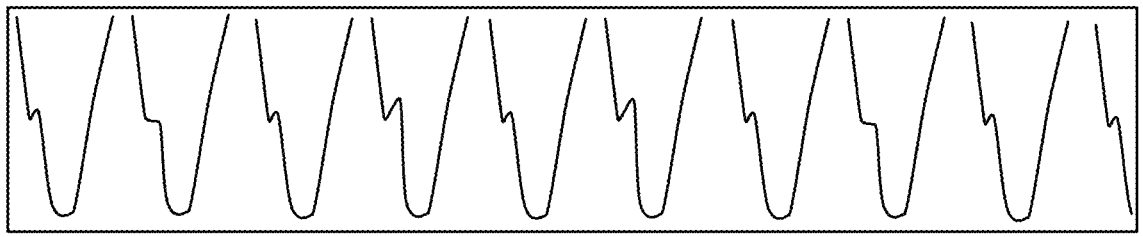
Figure 19C:
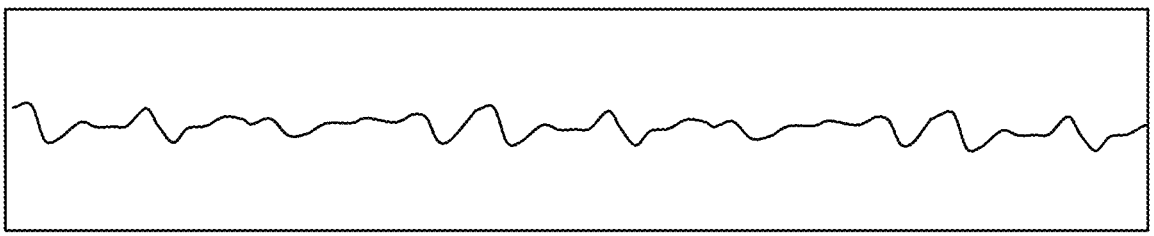

As shown in FIGS. 17 and 20, Block S222 recites: generating a delayed pulse signal dataset, which functions to delay one or more signals in order to improve signal quality deficiencies (e.g., signal saturation as shown in FIG. 19B, weak signals as shown in FIG. 19C, noisy signals, etc.). Block S222 can additionally or alternatively include determining a delay setting and/or updating a delay setting.

Block S222 preferably includes generating a delayed signal dataset from generated signal datasets generated at a signal generator, but any suitable signal dataset can be delayed. Delayed signal datasets are preferably transmitted to a distinct signal modification module (e.g., a detector module), but can additionally or alternatively be transmitted to an RF sensor device for transmission as incident signals, and/or transmitted to any suitable component.

Block S222 preferably includes generating a delay pulse signal dataset (e.g., at a delay module of the RF system) based on delaying a pulse signal dataset with a delay setting (e.g., delay value, delay line selection for a set of delay lines) for modifying pulse signal amplitude to be within a predetermined range of a target signal amplitude. The target signal amplitude can be predetermined (e.g., manually determined), automatically determined (e.g., based on preliminary biometric measurement results, based on supplemental sensor datasets such as motion sensor data indicating user motion, etc.), and/or otherwise determined. For example, determining a target signal amplitude can be based on a maximum signal amplitude processable by a signal modification module. In a specific example, determining a target signal amplitude can be based on a proportion (e.g., 60%) of the maximum input signal amplitude processable by a converter module (e.g., an analog-to-digital converter module). Additionally or alternatively, delay settings can be configured for modifying any suitable signal characteristic to improve signal quality.

Determining a delay setting can be performed continuously (e.g., on a pulse-to-pulse basis), periodically (e.g., at predetermined time intervals), in response to satisfaction of one or more conditions (e.g., a reflected signal exceeding a threshold amplitude, a biometric measurement result outside a value range, detection of a saturated signal amplitude, a weak signal amplitude, a noisy signal amplitude, etc.) and/or at any suitable time and frequency. Determining a delay setting is preferably performed at the processing and control system, but can additionally or alternatively be performed at any suitable component. In a example, Block S222 can include, at the processing and control system: determining one or more delay settings, and transmitting the one or more delay settings to one or more delay modules for generating a delayed signal dataset.

In a variation, Block S222 can include: determining a signal parameter (e.g., signal amplitude parameter, pulse parameter, etc.) describing one or more signals of a signal dataset. In examples, determining a signal parameter can include inputting a signal dataset into a converter module (e.g., input an analog signal in the range of −3.3V to 3.3V into an analog-to-digital convert); converting the signal dataset to digital values (e.g., in the range between 0 to 2^16) with the converter module; and determining the signal parameter based on analyzing the digital values to determine frequency components and/or timing characteristics. In an example, Block S222 can include detecting a saturated signal amplitude in response to a signal amplitude parameter indicating a maximum amplitudes above a first pre-defined threshold (e.g. 42K). In another example, Block S222 can include detecting a weak signal amplitude in response to a signal amplitude parameter indicating a maximum amplitude is below a second pre-defined threshold (e.g. 39K). In another example, Block S222 can include detecting a noisy signal in response to a signal parameter indicating a number of frequency components above a third pre-defined threshold and/or in response to a variance between the timing characteristics. However, determining a signal parameter can be performed in any suitable manner.

In another variation, Block S222 can include: updating a delay setting based on one or more signal parameters. In an example, updating a delay setting can include increasing an initial delay value in response to a signal amplitude parameter (e.g., generated for reflected signal dataset, for a modified sign al dataset, for a conditioned signal dataset, etc.) indicating saturated signal amplitude. In another example, updating the delay setting can include decreasing the initial delay value in response to the amplitude parameter indicating weak signal amplitude. In another example, updating the delay setting can include increasing the initial delay value in response to the signal parameter indicating a noisy signal. In a specific example, Block S222 can include: generating a subsequent amplitude-adjusted pulse signal dataset (e.g., subsequent to determining an initial biometric measurement result based on an initial amplitude-adjusted pulse signal dataset) based on the delay value; determining a subsequent signal amplitude parameter describing the subsequent amplitude-adjusted pulse signal dataset; and in response to the subsequent signal amplitude parameter being outside the predetermined range of the target amplitude, updating the delay value to a modified delay value; and updating the biometric measurement result (e.g., an initial cardiovascular parameter) based on an updated amplitude-adjusted pulse signal dataset generated based on the modified delay value. In another specific example, updating the delay value can include modifying the delay setting by an increment (e.g., where the preceding increment can be divided by half upon every iteration); generating a delayed signal dataset with the updated delay value; comparing a signal amplitude parameter for signals derived from the delayed signal dataset to a signal amplitude parameter condition (e.g., a signal amplitude within a predetermined range of a target signal amplitude); and repeating the preceding steps until the signal amplitude parameter satisfies the signal amplitude parameter condition.

In another specific example, a delay value is initially set at a predetermined baseline value. Upon detection of a saturated, weak, or noisy signal, delay optimization unit 137 adjusts the delay value according to a fixed amount at fixed time intervals. The process can be terminated in response to the average signal amplitude falling within a predetermined range of the target signal amplitude without exceeding it. In another specific example, the delay values is continuously updated until the average signal average signal amplitude (e.g., over a predetermined time period, etc.) is within a predetermined range to the target signal amplitude without exceeding it. The updating process can proceed continuously until signal acquisition is terminated In another specific example, Block S222 can include deriving one or more signal-related data features (e.g., amplitude features, frequency features, supplemental sensor data features such as motion data features, biometric measurement result features, pulse parameter features) based on signals derived from a first delayed signal dataset with a first delay value, the first delayed signal dataset associated with a first time period; updating the first delay value to a second delay value by processing the signal-related data features with a signal quality model (e.g., a machine learning model); using the second delay value to generate a second delayed signal dataset during a second time period subsequent the first time period; generating a biometric measurement result from signals derived from the second delayed signal dataset. However, updating a delay value can be performed in any suitable manner.

In a variation, Block S222 can include: generating a first delayed pulse signal dataset using a first delay setting, and generating a second delayed pulse signal dataset using a second delay setting. Generating the first and second delayed pulse signal datasets can be performed at a same delay module, different delay modules, and/or at any suitable components. Generating the first and second delayed pulse signal datasets are preferably performed substantially concurrently, but can be performed in serial and/or with any suitable temporal relationship. Generating the delayed pulse signal dataset preferably includes determining the first delay setting independently from delaying the second delay setting, but can alternatively be determined with a dependence relationship (e.g., determining a first delay value, generating a signal parameter describing signals derived from a delayed signal dataset associated with the first delay value, and determining the second delay value based on the signal parameter), and/or any suitable relationship. In an example, Block S222 can include determining at a processing and control system: a first delay value for a first receiver chain (e.g., including one or more of a first receiver block, a first delay module, a first detector module, a first amplifier, a first converter module, etc.), and a second delay value for a second receiver chain (e.g., including one or more of a second receiver block, a second delay module, a second detector module, a second amplifier, a second converter module, etc.). However, any suitable number of delayed pulse signal datasets can be generated in any suitable number of receiver chains and/or in any suitable manner.

Additionally or alternatively, generating a delayed pulse signal dataset can be performed in any suitable manner.

4.2.B Generating a Detected Signal Dataset.

As shown in FIG. 17, Block S224 recites: generating a detected pulse signal database, which functions to generate signals based on a change (e.g., phase, frequency, amplitude, time delay, etc.) between two or more signals (e.g., by mixing two or more signals).

Block S224 preferably includes detecting a change between a set of constituent signals (e.g., from mixing a set of constituent signals including one or more delayed signals). For example, Block S224 can include: in response to collecting the reflected pulse signal dataset and generating the delayed pulse signal dataset, mixing the reflected pulse signal dataset and the delayed pulse signal dataset, thereby generating a phase detected pulse signal dataset. Mixing a set of constituent signals preferably includes generating a detected signal dataset possessing one or more frequency parameters distinct from one or more frequency parameters associated with the set of constituent signals. However, generating a detected signal dataset can include generating detected signals possessing modified signal parameters typifying any suitable signal parameter type.

Block S224 preferably includes transmitting a detected signal dataset to one or more conditioning modules (e.g., an amplification module), but can additionally or alternatively include transmitting a detected signal dataset to the processing and control system and/or any other suitable component. However, generating a phase pulse signal dataset can be performed in any suitable manner.

4.2.C Generating a Modulated Signal Dataset.

As shown in FIG. 17, Block S226 recites: generating a modulated pulse signal dataset, which functions to modify one or more signal parameters of a signal dataset.

Generating a modulated signal dataset preferably includes modifying one or more of: signal frequency parameter, signal envelope parameter, signal amplitude parameter (e.g., based on modifying a signal frequency parameter), and/or any other suitable signal parameter.

Generating a modulated signal dataset is preferably from signal datasets generated by a pulse signal generator, but can be from any suitable signal datasets (e.g., a delayed signal dataset). Generating a modulated signal dataset preferably includes transmitting the modulated signal dataset to an RF sensor device (e.g., for transmission as incident signals), but can additionally or alternatively include transmitting modulated signal datasets to a different signal modification module (e.g., a delay module, a detector module, etc.), and/or any suitable datasets.

Generating a modulated pulse signal dataset is preferably performed at a pulse shaper module (e.g., a pulse width modulator), but can additionally or alternatively be performed at any suitable component.

In variation, Block S226 can include updating a pulse shaper parameter for a pulse shaper module. Updating the pulse shaper parameter is preferably in response to satisfaction of a signal parameter condition. For example, in response to a signal amplitude parameter exceeding a threshold value (e.g. saturated), the pulse shaper parameter can be modified to increase the frequency of a signal dataset (e.g., frequency of a damped sinusoidal envelope) to reduce signal amplitude of a reflected signal dataset and/or other signal dataset. In other examples, updating a pulse shaper parameter can be performed in response to detecting a saturated, weak, and/or noisy signal. Updating a pulse shaper parameter can be continually performed until a signal parameter falls into a predetermined range of a target signal parameter (e.g., a signal amplitude falling into a predetermined range of a target signal amplitude without exceeding it).

Updating a pulse shaper parameter can be performed at the processing and computing system and/or any suitable component. However, updating a pulse shaper parameter can be carried out analogously to updating a delay value (e.g., in Block S222), and/or in any suitable manner. Additionally or alternatively, generating a modulated pulse signal dataset can be performed in any suitable manner.

4.3 Generating a Biometric Measurement Result

As shown in FIG. 17, Block S230 recites: generating one or more biometric measurement results based on one or more pulse parameters derived from the modified pulse signal dataset, the biometric measurement result indicating the health of the user. Block S230 functions to analyze signal-related data to determine one or more metrics (e.g., biometric measurement results) assessing the physiological health of the user. Generating the one or more biometric measurement results can additionally or alternatively include: conditioning one or more pulse signal datasets (e.g., a reflected pulse signal dataset), generating one or more pulse parameters describing pulse signals derived from the reflected pulse signal dataset, filtering signal-related data outliers, and/or weighting signal-related data.

Biometric measurement results can include any one or more of: cardiovascular parameters, medical diagnoses, recommended treatments, respiratory parameters, tissue parameters, immune system parameters, digestive system parameters, endocrine system parameters, and/or any other suitable physiological parameters. Cardiovascular parameters can include any one or more of: blood pressure parameters (e.g., instantaneous blood pressure, blood pressure variability, etc.), measures indicative of atherosclerosis or other cardiovascular disease, heartbeat parameters (e.g., instantaneous heart rate, heart rate variability, average heart rate, resting heart rate, heartbeat signature, etc.), pulse rate parameters (e.g., instantaneous pulse rate, pulse rate variability, etc.), physical activity parameters (e.g., motion metrics, fitness metrics, etc.), parameters correlated with cardiovascular-related health (e.g., sleep metrics, etc.), vital signs, pulse oximetry metric, measures of arterial stiffness, associated respiration parameters (e.g., respiratory rate, respiratory patterns, etc.), and/or any other suitable metric relating to cardiovascular-related health.

Generating one or more biometric measurement results is preferably based on one or more pulse parameters (e.g., determined in Block S234), but can be additionally or alternatively based on supplementary sensor datasets, user-related data, and/or other suitable data.

In a variation, generating biometric measurement results includes generating one or more cardiovascular parameters based on one or more pulse parameters (e.g., which can be correlated to cardiovascular parameters). In an example, a pulse wave velocity can be used in calculating a blood pressure parameter. In a specific example, a blood pressure parameter can be calculated from PWV based on physics and conservation of energy, using: $BP = \cdot PWV^2 + B$ where A is related to a subject's height (e.g., which can be input by a user) and B is a constant. In another specific example, blood pressure can be calculated using:

$$BP = a \cdot \ln(PTT) + b$$
$$BP = a \cdot PWV + b$$
$$BP = \frac{a}{(PTT - c)^2} + b$$

where a, b, and c are constants derived using empirical regression.

In another specific example, the method can include generating a set of amplitude-adjusted pulse signal datasets within a 24-hour time period; determining a set of blood pressure parameters from the set of amplitude-adjusted pulse signal datasets, and determining a circadian blood pressure parameter for the set of blood pressure parameters, the circadian blood pressure parameter describing blood pressure over time (e.g., variability over a 24-hour period, blood pressure patterns, etc.)

In another variation, generating a cardiovascular parameter model for determining one or more cardiovascular parameters, based on features selected with machine learning algorithms. In this variation, feature-selection machine learning algorithms can be leveraged in determining features (e.g., derived from RF system-related data), affecting the determination of cardiovascular parameters.

In another variation, generating one or more biometric measurement results can include generating a medical diagnosis (e.g., of a cardiovascular condition) from one or more biometric measurement results (e.g., cardiovascular parameters). For example, generating a medical diagnosis can include generating a set of biometric measurement results (e.g., generated based on signal data collected over a day, multiple days, weeks, etc.), and processing the set of biometric measurement results with a over a period of times) medical diagnosis model.

Generating one or more biometric measurement results is preferably performed at a processing subsystem (e.g., retained in an RF system housing, a remote server, etc.) of a processing and control system, but can additionally or alternatively be performed at any suitable processing component (e.g., a processor of a distinct user device such as a user mobile phone communicably coupled with the RF system, etc.). In a variation, portions of generating one or more biometric measurement results can be allocated across a plurality of processing components. For example, generating preliminary biometric measurement results can be performed at a processing subsystem of the RF system, and filtering signal-related data and/or weighting signal-related data (e.g., to generate final biometric measurement results for presentation to a user) can be performed at a distinct user device (e.g., at a software application of a user's mobile phone) and/or a remote server (e.g., which can subsequently transmit the final results to the user at the software application). However, generating a pulse parameter can be performed in any other suitable manner.

4.3.A Conditioning a Signal Dataset.

Generating one or more biometric measurement result can additionally or alternatively include Block S232, which recites: conditioning one or more pulse signal datasets. Block S232 functions to condition one or more signal datasets for improving signal quality, converting signal data into a suitable form (e.g., analog-to-digital conversion) for processing in generating biometric measurement results.

Conditioning one or more signal datasets can include any one or more of: amplifying, filtering, converting, normalizing, noise reduction, smoothing, model fitting, transforming, and/or any suitable conditioning operation. Conditioning a signal dataset preferably includes conditioning a modified signal dataset (e.g., a delayed signal dataset, a phase detected signal dataset, etc.), but can additionally or alternatively include conditioning a reflected signal dataset, and/or any suitable signal dataset.

Conditioning the one or more signal datasets is preferably performed by one or more conditioning modules (e.g., amplification modules, filtering modules, converter modules, etc.), but can be performed by any suitable component. Conditioning the one or more signal datasets is preferably performed prior to receipt by the processing and control subsystem. For example, modified signal datasets including modified signals (e.g., modified pulse signals) can be input directly into a conditioning module. In a specific example, the method can include amplifying a phase detected signal dataset received directly from a detector module. Conditioning a signal dataset preferably includes transmitting the conditioned signal dataset to the processing and control subsystem, but can additionally or alternatively include transmission to any suitable entity (e.g., information module).

In a variation, the method can include conditioning a plurality of signal datasets at a plurality of conditioning chains each including one or more conditioning modules. For example, the method can include conditioning a first modified signal dataset at a first conditioning chain (e.g., including amplifying, filtering, and converting at a first set of conditioning modules), and conditioning a second modified signal dataset at a second conditioning chain (e.g., including amplifying, filtering, and converting at a second set of conditioning modules). Different conditioning chains can include the same, overlapping, or distinct conditioning operations, such that different sets of conditioning operations can be performed for the same and/or different signal datasets. However, conditioning one or more pulse signal dataset can be performed in any other suitable manner.

4.3.B Generating a Pulse Parameter.

Generating one or more biometric measurement results can additionally or alternatively include Block S234, which recites: generating one or more pulse parameters describing pulse signals derived from the reflected pulse signal dataset. Block S234 functions to illuminate one or more characteristics of signal-related data from which biometric measurement results can be determined.

Pulse parameters can include any one or more of: pulse transit time (PTT) (e.g., the time duration for an arterial pulse wave produced by a heartbeat to travel a specific distance along the artery), pulse wave velocity (PWV) (e.g., inversely related to PTT; the rate of propagation of an arterial pulse), pulse arrival time (PAT) (e.g., the time between an electrocardiogram ECG-R peak and the arrival of the corresponding pulse wave at a specified point in an artery), a pulse pressure parameter, orientation parameter (e.g., pulse orientation relative the artery), pulse frequency parameter, pulse depth parameter, pulse intensity parameter, and/or any other suitable pulse parameter.

Generating a pulse parameter is preferably based on pulse signals derived from the reflected pulse signal dataset (e.g., reflected pulse signal data, modified signal datasets, conditioned signal datasets, etc.), but can additionally or alternatively be based on supplemental sensor datasets, user-related data, and/or any other suitable data.

In a variation, generating a pulse parameter includes generating a PWV from a pulse signal dataset. In this variation, generating a PWV preferably includes generating a PWV based on a plurality of a pulse signal datasets. In a specific example, collecting a first reflected pulse signal dataset including pulse signals reflected in response to transmission of incident signals at a first RF sensor device; collecting a second reflected pulse signal dataset including pulse signals reflected in response to transmission of incident signals at a second RF sensor device separated from the first RF sensor device at a distance; determining a change in pulse return time based on pulse signals derived from the first and second reflected pulse signal datasets; and generating at least one of PWV and PTT based on the change in pulse return time and the distance between the first and second RF sensor devices. Additionally or alternatively, generating a PWV can include generating a PWV from a pulse signal dataset and a supplementary sensor dataset. For example, the method can include collecting a reflected pulse signal dataset at an RF sensor device of the RF system, receiving a supplemental sensor dataset (e.g., a photoplethysmography dataset, an ECG dataset, a Ballistocariography dataset, etc.) collected at a supplemental sensor module (e.g., at the RF system, at a distinct user device, etc.), and generating at least one of PWV and PTT based on processing the reflected pulse signal dataset with the supplemental sensor dataset.

In another variation, generating a pulse parameter can include generating a PTT based on a diastole-minimum approach, including: determining minimum values associated with pulse signals derived from the first and second reflected pulse signal datasets; determining time values associated with the minimum values, and determining the PTT based on a difference between a minimum value associated with a pulse signal derived from the first reflected pulse signal dataset and a minimum value associated with a pulse signal derived from the second reflected pulse signal dataset.

In another variation, generating a pulse parameter can include generating a PTT based on a tangential approach, including: for a first and a second pulse signal respectively derived from the first and second reflected pulse signal datasets: determining a maximum first derivative point (e.g., associated with a maximum rising slope), determining a minimum for the pulse signal, identifying an intersection between a line tangentially through the maximum first derivative point and a line tangential to the minimum of the corresponding pulse; determining a time value associated with the intersection; and generating a PTT based on a difference in the time value associated with the first pulse signal and the time value associated with the second pulse signal. In other variations, generating a PTT can be based on points of a maximum first derivative (e.g., a maximum first derivative approach), a maximum second derivative e.g., a maximum second derivative approach), and/or regions of the pules signal proximal the foot of the pulse signal (e.g., a diastole-patching approach). However, generating PWV and/or PTT can be performed in any suitable manner.

Generating a pulse parameter is preferably performed at a processing subsystem of the processing and control system, but can additionally or alternatively be partially or fully performed at any suitable processing component. Generating one or more pulse parameters can include generating a pulse parameter or set of pulse parameter for each pulse during a time period, for a subset of pulses during a time period, and/or for any suitable number of pulses. Generating a pulse parameter can be performed in real time on a pulse-by-pulse basis, in batch, and/or at any suitable frequency. However, generating a pulse parameter can be performed in any other suitable manner.

4.3.C Filtering Signal-Related Outliers.

Generating one or more biometric measurement results can additionally or alternatively include Block S236, which recites: filtering signal-related data outliers. Block S236 functions to filter outliers to determine biometric measurement results with increased accuracy. Filtering one or more outliers preferably includes filtering outliers from one or more: signal datasets (e.g. RF sensor device datasets, pulse signal datasets, supplementary sensor datasets, etc.), pulse parameters, biometric measurement results (e.g., cardiovascular parameters, etc.), and/or any other suitable data.

Figure 21:
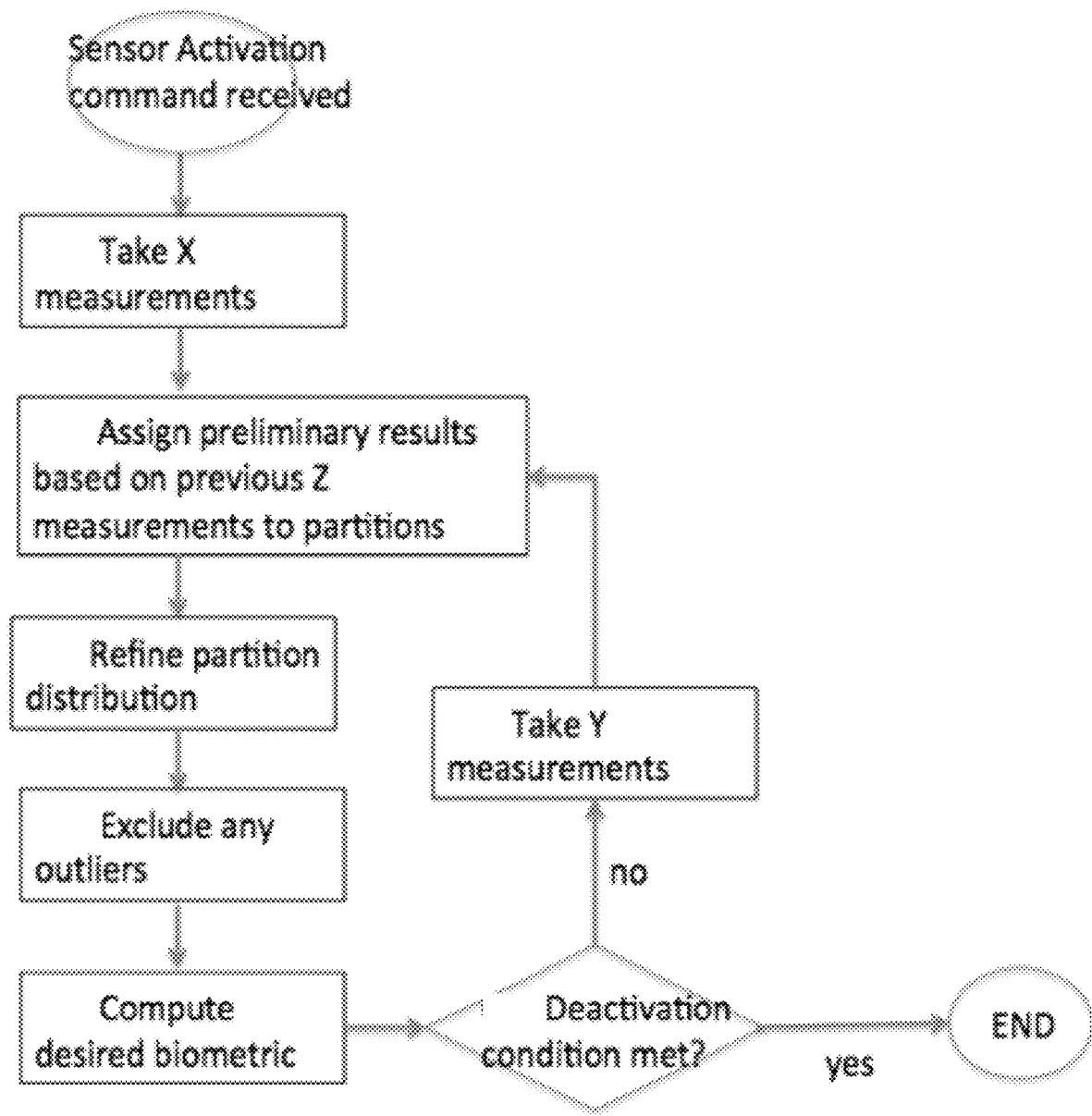
FIG. 21 is a flow chart representation of a variation of an embodiment of a method.

In a variation, as shown in FIG. 21, filtering one or more outliers based on partitions (e.g., pulse signal value partitions, pulse parameter partitions, cardiovascular parameter partitions, etc.). Partition ranges can be predetermined (e.g., manually by an RF system provider, by a user, etc.), automatically determined (e.g., employing machine learning techniques, etc.) and/or otherwise determined. Partition ranges can be determined based on aggregated (e.g., historical) RF system-related data, and/or any suitable data. For example, the activated sensor(s) can be operated to take X measurements where X is a predetermined scalar value if only RF biometric sensor 101 is activated (e.g. X=2 million measurements, X=measurements taken during a predetermined time period, for example, 2 seconds) or a predetermined vector value if more than one sensor is used (e.g. X=[4 million measurements for RF biometric sensor 101, 20 measurements for motion sensor], X=measurements taken during a predetermined time period for each sensor). Z measurement values can be used to derive preliminary biometric results. Z can be the same or different value from X. For example, measurement values from RF biometric sensor 101 can be used to determine heart rate and/or pulse transit time, which can be used to determine blood pressure. As another example, measurement values from motion sensors can be used to determine motion in 3D space. The preliminary results based on the previous Z measurements can be processed to eliminate outliers. For example, the preliminary results can be assigned to predetermined partitions. Each type of sensor can have its own predetermined partition sets. For example, a partition for systolic blood pressure can be {<90, 90 to 120, 120 to 140, >140}. Alternatively, a partition for systolic blood pressure can be {<90, [90,100), [100,110), [110,120), [120,130), [130,140), [140,150), [150,160), [160,170), >170}. Other partitions can be possible. The partitions for different sensors can be further refined. For example, given a subject's prior measurement history data, the partition range can be adjusted to better match the subject's own statistics. Measurement context information (e.g. before sleep, after rest, after exercise) can be used to determine a subject's partitions. As another example, the number of partition and/or each partition range can be adjusted such that the standard deviation of each partition is minimized. One or more adjusted partitions can be considered to be outliers and those preliminary results can be excluded. Such outlier rejection can apply to RF biometric sensor 101 and/or any other sensor. Final biometric results can be computed from the filtered signal dataset, and the final biometric measurement results can be presented to the user. However, filtering signal-related data outliers can be performed in any other suitable manner.

4.3.D Weighting Signal-Related Data

Generating one or more biometric measurement results can additionally or alternatively include Block S238, which recites: weighting signal-related data. Block S236 functions to evaluate contextual conditions describing the environment in which RF sensor device signals are acquired, in order to accordingly weight the signal-related data for generating biometric measurement results with greater accuracy.

Weighting signal-related data preferably includes assigning weights based on contextual data, including any one or more of: supplemental sensor data (e.g., motion sensor data, optical sensor data, etc.), user-related data (e.g., user demographics, weight, body shape, skin thickness, etc.). Weighting signal-related data can include weighting modified signal data, conditioned signal data, pulse parameters, biometric measurement results, partitioned data (e.g., as in Block S236), filtered data, and/or any suitable data. For example, the method can include: receiving a motion sensor dataset collected at the motion sensor during a time period, where an amplitude-adjusted pulse signal dataset corresponds to the time period; generating a weighting parameter for a temporal indicator (e.g., a time point, a time duration) within the time period, based on motion during the temporal indicator of the physiological region; generating a weighted pulse signal value from assigning the weighting parameter to a pulse signal value of the amplitude-adjusted signal dataset, the pulse signal value corresponding to the temporal indicator; determining the pulse parameter based on the weighted pulse signal value. In another example, each partition for a motion sensor (post outlier rejection) can be assigned a weighting parameter in the range of 0 to 1 where 0 represents excess motion and 1 represents minimal motion. Each corresponding preliminary result from RF biometric sensor 101 is weighed by a weighting parameter. The final biometric results can be computed by a weighted average across the preliminary results. However, weighting signal-related data can be performed in any other suitable manner.

4.4 Controlling Signal Acquisition Operation.

Figure 18:
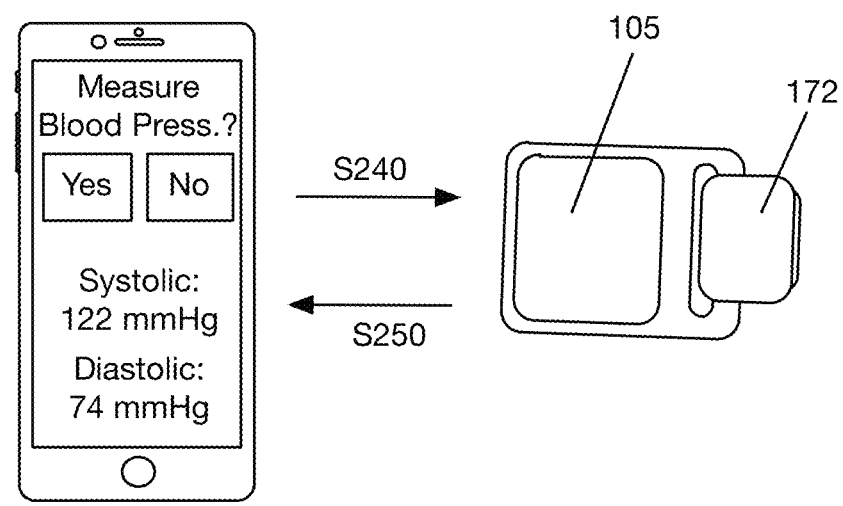
FIG. 18 is a schematic representation of a variation of an embodiment of a method.

As shown in FIGS. 17-18, the method can additionally or alternatively include Block S240, which recites: controlling signal acquisition operation. Block S240 functions to initiate, modify, and or terminate signal acquisition by one or more sensor modules (e.g., RF sensor device, supplemental sensor modules).

Controlling signal acquisition operation can additionally or alternatively include: activating signal acquisition, and/or deactivating signal acquisition. Controlling signal acquisition operation is can be performed in response to a manual trigger (e.g., a request by a user), automatic trigger (e.g., detecting a target physiological region within a threshold distance of the radio sensor module), and/or at any suitable time. Controlling signal acquisition operation is preferably performed by a processing and control subsystem communicably coupled to the one or more sensor modules, but can be performed by any suitable component.

Activating signal acquisition can, for example, be initiated by a user (either the subject or another user). In an example, a user can have positioned RF system near the target region. The data collection process can be initiated by user request via input module on the RF system. For example, in an example, a user can press a button on RF system to request biometric measurements. As another example, a user can select a software application on RF system via input module and follow instructions via output module 105 to request biometric measurements. In an example, a user can configure request settings provided by a software application on RF system. In another example, RF system can have default request settings that can or can not be at least partially configurable by a user. Activating signal acquisition can be immediately performed in response to receiving an activation request, but can be delayed (e.g., by a predetermined period of time displayed to the user) and/or otherwise performed at any suitable time in relation to the activation request. A request can include multiple request instances (e.g. a periodic request with individual request instances at fixed time intervals). Each request instance can generate a separate process flow as shown in FIG. 7.

Receiving signal acquisition requests can include receiving a time-based request, context-based request, and/or a combination of both. A time-based request can be a one-time request (e.g. once immediately, once at noon, once at 5 pm), periodic request (e.g. once every morning and once every evening, once every 30 minutes, once every minute), recurrent request (e.g. once every Monday and once every Friday, 5 times today, 10 times this week), or scheduled request (e.g. one time on September 22nd, within 24 hours before next check-up on October 1st). The scheduled time can be based on network synchronized system time. If a user or subject changes time zones, the system time can be changed automatically. A user can be alerted to adjust scheduled requests when a change in time zone is detected. In an example, a user is alerted if the scheduled time is not within a normal operating time range (for example, if a prior 9 pm measurement is now scheduled to take place at 2 am due to time zone adjustment). The user can click on the alert message to reconfigure measurement schedules. In another example, a prior 9 pm measurement remains 9 pm in the new time zone. The user can be notified and asked to confirm. In an example, a more suitable time can be recommended to the user and the user can confirm or cancel the recommended schedule.

A context-based request can be dependent on the state of motion of the subject (e.g. after exercise, before sleep, after awaking, while sitting, while running), location-based (e.g. at the doctor's office, at home), environment-based (e.g. heightened ambient noise, above average number of unread messages, presence of information within the subject's social network that can negatively affect the subject's health, presence of information within the subject's field of view that can negatively affect the subject's health). A request can combine any number of time and context-based request (e.g. once every 15 min after exercise for 2 hours, 5 measurements while sitting at the doctor's office, whenever the target is substantially stationary for a predetermined amount of time, every 2 hours and whenever there is information within the subject's field of view that can negatively affect the subject's health). As an example, a biometric measurement request can be scheduled to occur every morning at 8 am. A notification can appear on RF system and/or a paired electronic device (e.g. mobile phone) a predetermined time prior to the scheduled time and/or at the scheduled time. A user can click on the notification to launch a software application to commence biometric measurements. Alternatively, the user can launch a software application upon receiving the notification.

In a variation, Block S240 can include initiating signal acquisition in response to receiving a signal acquisition request communication from a user device in communication contact with RF system. For example, in an example, a user can request biometric measurement via hardware trigger or software on a mobile phone in communication contact with RF system. In another example, a mobile phone can contain default request settings for RF system which can or can not be configurable by a user. In an example, a user can configure request settings provided by a software application on a device in communication contact with RF system. In an example, the data collection process can be initiated by a third party user (e.g. doctor) either by operating RF system directly or remotely through a remote control unit or through a communication network. In another example, a user (possibly doctor, nurse, care-taker, family member, service provider, etc.) can request biometric measurement of a subject and/or configure request settings via a device in communication contact with RF system through a communication network. In an example, entities authorized to use information module 158 or entities with access to services provided by information module can request biometric data measurements from RF system and/or configure request settings. In an example, RF system, a device in communication contact with RF system, or another user can send a reminder to take measurements for a subject.

In another variation, Block S240 can include activating signal acquisition in response to an analysis of a pulse parameter satisfying one or more conditions (e.g., a pulse wave velocity within a predetermined range). In this variation, the method can include continually determining pulse parameters; generating analyses of the pulse parameters; and comparing the pulse parameters against the condition until a pulse parameter meets the condition.

Figure 22:
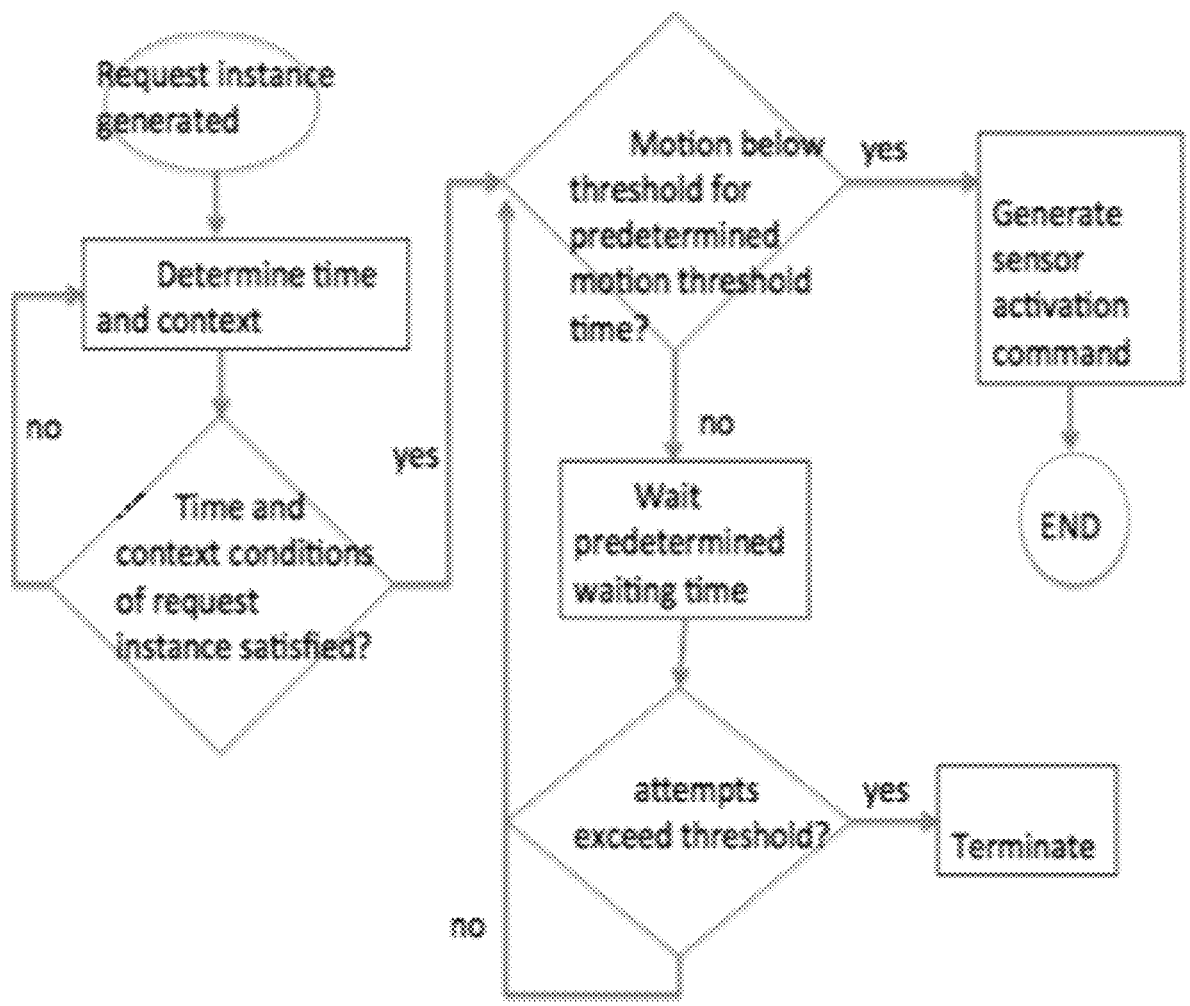
FIG. 22 is a flow chart representation of a variation of an embodiment of a method.

In another variation, as shown in FIG. 22, Block S240 can include activating signal acquisition in response to context conditions (e.g., supplemental sensor data) satisfying threshold criteria. Context conditions can be determined, for example, using other sensor(s) 102 or from other context information related to the subject, the target, or RF system, or any combination of the above. The device performing the activation process can make a determination as to whether or not the requested time and context conditions of the current request instance are satisfied. In a specific example, analyzing context conditions includes analyzing supplemental motion sensor data. A determination can be made as to whether motion data is below a predetermined threshold for a predetermined motion threshold duration (e.g., seconds, minutes, etc.). The motion data can be determined, for example, using RF system motion sensor and/or from motion sensors on a device communicating with RF system. Analyzing context conditions can be performed continually, periodically (e.g., waiting a predetermined waiting period after an initial analysis of context conditions fails to meet the threshold criteria, etc.). Upon termination of an activation request, feedback can be sent to the user. For example, the user can be notified of the failed request instance, a warning can be issued, the failure can be logged, further instructions can be issued to the user to remain stationary, and/or an option to re-issue or re-configure the request can be presented to the user. In a specific example, the method can include: receiving a preliminary motion sensor dataset collected at a motion sensor of the RF system during a first time period, the preliminary motion sensor dataset describing motion during the first time period of a physiological region proximal the artery of the user; determining a time duration during which the motion is below a motion threshold, based on the motion sensor dataset, where the time duration is within the first time period; where collecting the reflected pulse signal dataset (e.g., activating signal acquisition for determining biometric measurement results) is in response to the time duration satisfying a time condition.

Deactivating sensor acquisition can be in response to satisfaction of a deactivation condition. In an example, the RF biometric sensor 101 takes measurements for a fixed duration of time (e.g. 15 seconds). In another example, RF biometric sensor 101 takes measurements until receiving a sensor deactivation command (e.g. from a user) to stop taking measurements. In another example, RF biometric sensor 101 takes measurements until a measurement value within error tolerance is obtained. In another example, RF biometric sensor 101 deactivates if a pulse is not detected for a predetermined period of time during the measurement process. In another example, RF biometric sensor 101 deactivates if the number of inadequate measurements exceeds a predetermined threshold. In another example, a combination of different termination/deactivation conditions is possible. The termination/deactivation conditions can be available as options for the user to select. If deactivation condition is met, then the process ends; otherwise, at step 607 another Y measurements are taken and the process goes back to 602. X, Y, Z can be the same or different values.

4.5 Outputting RF System-Related Information.

As shown in FIGS. 17-18, the method can additionally or alternatively include Block S250, which recites: outputting RF system-related information to the user. Block S250 functions to present RF system-related information (e.g., biometric measurement results) to the user to inform the user of parameters indicating their health and/or to inform the user of RF system operation.

Outputted information preferably include one or more biometric measurement results including systolic blood pressure, diastolic blood pressure, and/or pulse rate. Irregular pulse rate can also be detected and displayed. Additionally or alternatively, outputting information can include outputting an interpretation of the biometric measurement results (e.g. show user how their biometric measurement results compare against average, indication of potential health issues, alert if critical condition is detected). A user can be presented with calibrated values for biometric results had the measurements been taken at a different location. For example, if the measurements are taken at the wrist, a user can be presented with results calibrated for measurements at the arm (e.g., taking into consideration a subject's arm length).

In examples, a high watermark, low watermark, mean, median, mode, and/or range can be calculated for each measured value for a single measurement process or a group of measurement processes. The user can preconfigure the number of measurement results to average over or select the number of measurement results to average over. The user can also preconfigure the duration between successive measurement results for averaging purposes. A user can review historical measurement results in a list or chart format.

The resulting data can be presented in a visual form that highlights correlations and trends in the results across individual measurements or groups of measurements. The result value correlates to an indicated position on a color-coded graph (green to red), which is representative of normal blood pressure, pre-hypertension, stage 1 hypertension, and stage 2 hypertension for the diastolic it's normal, low, too low, dangerously low. For example, for Systolic blood pressure: Stage 2 Hypertension>=160; Stage 1 Hypertension 140-159; Prehypertension 120-139; Normal 90-119; Low 60-89; Too Low 50-59; Dangerous Low<50. For Diastolic: Stage 2 Hypertension>=100; Stage 1 Hypertension 90-99; Prehypertension 80-89; Normal 60-79; Low 40-59; Too Low 33-39; Dangerous Low<33. This provides an intuitive visual indicator to see where the BP range fits within the standards. The color-code can correspond to standard color indicators established by the World Health Organization, American Heart Association, European Society of Hypertension, or other standard bodies, or associations/societies). The graphs can be dynamic. For example, the colors can be used to indicate where the subject's normal range is based on his/hers previous measurement results, averages and/or standard deviations. The normal range determination can depend on the context (e.g. previous averages at approximately the same time of day, after waking up, evening, etc.). The graphs can be a time series showing biometric results over time. A user can zoom in and out of a graph to see finer granularity of data and/or to see more data. Biometric trends, conditions, predictions, and/or recommendations can be output to the user. Because RF system and/or information module can collect biometric results from multiple subjects, a comparison between subjects can be made and an indication of how a particular subject's biometric data compares with others (e.g. all subjects, within an age group, within a gender group, etc.) can be presented. In an example, an analytics application can access data stored in information module to perform population wide disease and health condition analyses. Such analyses can include disease trends within the entire population or across population segments.

In a variation, data from multiple sensors can be correlated for display to the user. These correlations can be used to provide context for the measured biometric, such as the activity level of the subject before and/or during the biometric measurement, whether the subject consumed food or drink beforehand, whether the subject was stressed beforehand, whether the subject was sleeping beforehand, etc.

In another variation, Block S150 can include outputting information about measurement progress and status are output to the user (e.g., during signal acquisition). In an example, if a measured result indicates abnormal or critical condition, the user can be alerted and reminded to repeat the measurement after a predetermined time. The predetermined time depends on the biometric being measured. Depending on the condition, if multiple successive measurement results indicate abnormal or critical conditions, the user can be alerted to contact appropriate medical personnel. In an example, medical personnel, and/or a preselected list of people or entities is alerted automatically.

In another variation, Block S150 can include receiving user-added information regarding a biometric measurement result. For example, Block S150 can include receiving contextual information such as what the subject (could be the same person as the user or a different person) is feeling, has been doing, etc. prior to or during the measurement. A user can also add measurement data or results from a different biometric measurement device manually through an application and the input module. Each measurement and/or results is associated with a time stamp at which the measurement was taken. The date and time information for the time stamp can be obtained from a system clock, which can be synchronized with system time.

In another variation, outputting RF system-related information can include outputting an RF system-related notification. Notifications can be configured in information module, a companion application, or on the RF system. Notifications can trigger when specific conditions are met, including any one or more of: a measurement has not been taken within a specific time period, a scheduled measurement has not occurred, a measured value is outside a range of historical values, a measured value falls within or outside a predefined range, and/or any other suitable conditions. However, outputting RF system-related information can be performed in any suitable manner.

The method and/or system of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a patient computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, though any suitable dedicated hardware device can (alternatively or additionally) execute the instructions.

The FIGURES illustrate the architecture, functionality and operation of possible implementations of systems, methods and computer program products according to preferred embodiments, example configurations, and variations thereof. In this regard, each block in the flowchart or block diagrams can represent a module, segment, step, or portion of code, which includes one or more executable instructions for implementing the specified logical function(s). It should also be noted that, in some alternative implementations, the functions noted in the block can occur out of the order noted in the FIGURES. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the embodiments of the invention without departing from the scope of this invention as defined in the following claims.

We claim:

1. A method for evaluating pulse wave velocity (PWV) of a user, the method comprising:
   providing an RF system with a first RF sensor and a second RF sensor, each RF sensor having an antenna that transmits an incident RF signal and an antenna that senses reflected RF signals, wherein the first RF sensor and the second RF sensor are placed facing an artery of the user and spaced apart in the direction of the artery a known distance;
   at each of the first RF sensor and the second RF sensor, collecting a reflected pulse signal dataset comprising signals reflected in response to signal transmission by the respective RF sensor towards the artery of the user;
   generating a first delayed pulse signal dataset based on delaying the pulse signal dataset from the first RF sensor with a delay setting and generating a second delayed pulse signal dataset based on delaying the pulse dataset from the second RF sensor with the delay setting;
   in response to collecting the first and second reflected pulse signal datasets and generating the first and second delayed pulse signal datasets, generating first and second detected pulse signal datasets based on the reflected signal datasets and the delayed signal datasets;
   generating first and second amplitude-adjusted pulse signal datasets based on conditioning the first and second detected pulse signal datasets; and
   determining a value for the pulse wave velocity of the user based on the first and second amplitude-adjusted pulse signal datasets, wherein the determined value of the pulse wave velocity is based on arterial motion of the artery and determined from a calculated change in pulse return time based on the first and second amplitude-adjusted pulse signal datasets and the known distance that the first and second RF sensors are spaced apart in the direction of the artery.

2. The method of claim 1, further comprising, for each of the first and second reflected pulse signal datasets and prior to collecting the first and second reflected pulse signal datasets:
   collecting an initial reflected pulse signal dataset comprising initial signals reflected in response to initial signal transmission by the RF system towards the user;
   generating an initial delayed signal dataset from delaying an initial signal dataset with an initial delay setting;
   generating an initial amplitude-adjusted signal dataset based on the initial reflected signal dataset and the initial delayed signal dataset;
   determining a signal amplitude parameter describing the initial amplitude-adjusted signal dataset; and
   updating the initial delay setting to the delay setting based on the signal amplitude parameter.

3. The method of claim 2, wherein updating the initial delay setting comprises increasing the initial delay setting in response to the signal amplitude parameter indicating saturated signal amplitude.

4. The method of claim 2, wherein updating the delay setting comprises decreasing the initial delay setting in response to the amplitude parameter indicating weak signal amplitude.

5. The method of claim 1, further comprising:
   receiving a preliminary motion sensor dataset collected at a motion sensor of the RF system during a first time period, the preliminary motion sensor dataset describing motion during the first time period of a physiological region proximal the artery of the user;
   determining a time duration during which the motion is below a motion threshold, based on the motion sensor dataset, wherein the time duration is within the first time period;
   wherein collecting the reflected signal dataset is in response to the time duration satisfying a time condition.

6. The method of claim 1, further comprising:
   providing the RF system at a physiological region proximal the artery;
   generating a set of signals with a signal generator of the RF system; and
   transmitting an incident signal derived from the set of signals with an antenna of the RF system,
   wherein the signal dataset comprises the incident signal.

* * * * *